US011660427B2

(12) United States Patent
McGowan et al.

(10) Patent No.: US 11,660,427 B2
(45) Date of Patent: May 30, 2023

(54) SUPERHEATING SYSTEM FOR INERTIAL IMPULSE GENERATION TO DISRUPT VASCULAR LESIONS

(71) Applicant: Boston Scientific Scimed, Inc., Maple Grove, MN (US)

(72) Inventors: Roger W. McGowan, Otsego, MN (US); Daniel Frank Massimini, Brooklyn Park, MN (US); Christopher Smuk, Champlin, MN (US); Haiping Shao, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 388 days.

(21) Appl. No.: 16/879,635

(22) Filed: May 20, 2020

(65) Prior Publication Data

US 2020/0398033 A1 Dec. 24, 2020

Related U.S. Application Data

(60) Provisional application No. 62/865,524, filed on Jun. 24, 2019, provisional application No. 62/865,507, filed on Jun. 24, 2019.

(51) Int. Cl.
*A61M 25/10* (2013.01)
*H05B 6/10* (2006.01)

(52) U.S. Cl.
CPC ....... *A61M 25/10184* (2013.11); *H05B 6/108* (2013.01)

(58) Field of Classification Search
CPC ..... A61B 18/20; A61B 18/201; A61B 18/245; A61B 18/26; A61B 2018/00023;
(Continued)

(56) References Cited

U.S. PATENT DOCUMENTS 4,649,924 A 3/1987 Taccardi
4,699,147 A 10/1987 Chilson et al.
(Continued)

FOREIGN PATENT DOCUMENTS

AU 2017205323 1/2022
AU 2019452180 1/2022
(Continued)

OTHER PUBLICATIONS

International Search Report and Written Opinion dated Jun. 2, 2021 in PCT Application Serial No. PCT/US2021/018522.
(Continued)

*Primary Examiner* — Robert A Lynch
(74) *Attorney, Agent, or Firm* — Roeder & Broder LLP; James P. Broder

(57) ABSTRACT

A catheter system for imparting pressure to induce fractures in a vascular lesion within or adjacent a vessel wall, includes a catheter and a superheating system. The catheter can advance to the vascular lesion. The catheter includes an elongate shaft and a balloon coupled to the elongate shaft. The balloon includes a balloon wall. The balloon moves between a collapsed configuration and a first expanded configuration suitable for anchoring the catheter in position relative to a treatment site. The superheating system can heat a balloon fluid within the balloon rapidly enough to achieve spontaneous vaporization of the balloon fluid and to generate inertial bubbles and acoustic pressure waves. The superheating system can include a first light guide extending along the elongate shaft. The first light guide is in optical communication with a light source at a proximal portion of the first light guide.

20 Claims, 16 Drawing Sheets

(58) Field of Classification Search
CPC .. A61B 2018/0022; A61B 2018/00285; A61B 2018/00404; A61B 2018/00577; A61B 2018/00625; A61B 2018/2035; A61B 2018/2261; A61B 2018/2272; A61B 2018/2277; A61B 2018/2294; A61B 2018/263; A61B 2018/266; A61M 25/10184; A61N 2007/0039; A61N 2007/0043; H04B 6/108
See application file for complete search history.

(56) References Cited

U.S. PATENT DOCUMENTS

| | | |
|---|---|---|
| 4,799,479 A | 1/1989 | Spears |
| 4,913,142 A | 4/1990 | Kittrell et al. |
| 4,955,895 A | 9/1990 | Sugiyama |
| 4,960,108 A | 10/1990 | Reichel et al. |
| 4,994,059 A | 2/1991 | Kosa et al. |
| 5,034,010 A | 7/1991 | Kittrell et al. |
| 5,041,121 A | 8/1991 | Wondrazek et al. |
| 5,104,391 A | 4/1992 | Ingle |
| 5,116,227 A | 5/1992 | Levy |
| 5,152,768 A | 10/1992 | Bhatta |
| 5,173,049 A | 12/1992 | Levy |
| 5,181,921 A | 1/1993 | Makita et al. |
| 5,200,838 A | 4/1993 | Nudelman |
| 5,290,277 A | 3/1994 | Vercimak et al. |
| 5,372,138 A | 12/1994 | Crowley |
| 5,400,428 A | 3/1995 | Grace |
| 5,422,926 A | 6/1995 | Smith |
| 5,454,809 A | 10/1995 | Janssen |
| 5,509,917 A | 4/1996 | Cecchetti |
| 5,540,679 A | 7/1996 | Fram |
| 5,562,657 A | 10/1996 | Griffin |
| 5,598,494 A | 1/1997 | Behrmann et al. |
| 5,609,606 A | 3/1997 | O'Boyle |
| 5,611,807 A | 3/1997 | O'Boyle |
| 5,697,377 A | 12/1997 | Wittkampf |
| 5,718,241 A | 2/1998 | Ben-Haim et al. |
| 5,729,583 A | 3/1998 | Tang |
| 5,772,609 A | 6/1998 | Nguyen et al. |
| 5,891,135 A | 4/1999 | Jackson et al. |
| 5,906,611 A | 5/1999 | Dodick et al. |
| 5,944,687 A | 8/1999 | Benett et al. |
| 6,080,119 A | 6/2000 | Schwarze et al. |
| 6,123,923 A | 9/2000 | Unger |
| 6,139,510 A | 10/2000 | Palermo |
| 6,186,963 B1 | 2/2001 | Schwarze et al. |
| 6,203,537 B1 | 3/2001 | Adrian |
| 6,210,404 B1 | 4/2001 | Shadduck |
| 6,339,470 B1 | 1/2002 | Papademetriou et al. |
| 6,368,318 B1 | 4/2002 | Visuri et al. |
| 6,500,174 B1 | 12/2002 | Maguire et al. |
| 6,514,203 B2 | 2/2003 | Bukshpan |
| 6,514,249 B1 | 2/2003 | Maguire |
| 6,524,251 B2 | 3/2003 | Rabiner et al. |
| 6,538,739 B1 | 3/2003 | Visuri et al. |
| 6,607,502 B1 | 8/2003 | Maguire et al. |
| 6,652,547 B2 | 11/2003 | Rabiner et al. |
| 6,666,834 B2 | 12/2003 | Restle et al. |
| 6,773,447 B2 | 8/2004 | Laguna |
| 6,849,994 B1 | 2/2005 | White et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,309,324 B2 | 12/2007 | Hayes et al. |
| 7,470,240 B2 | 12/2008 | Schultheiss et al. |
| 7,569,032 B2 | 8/2009 | Naimark et al. |
| 7,599,588 B2 | 10/2009 | Eberle et al. |
| 7,713,260 B2 | 5/2010 | Lessard |
| 7,758,572 B2 | 7/2010 | Weber et al. |
| 7,810,395 B2 | 10/2010 | Zhou |
| 7,850,685 B2 | 12/2010 | Kunis et al. |
| 7,867,178 B2 | 1/2011 | Simnacher |
| 7,972,299 B2 | 7/2011 | Carter |
| 7,985,189 B1 | 7/2011 | Ogden et al. |
| 8,162,859 B2 | 4/2012 | Schultheiss et al. |
| 8,166,825 B2 | 5/2012 | Zhou |
| 8,192,368 B2 | 6/2012 | Woodruff |
| 8,292,913 B2 | 10/2012 | Warnack |
| 8,364,235 B2 | 1/2013 | Kordis et al. |
| 8,419,613 B2 | 4/2013 | Saadat |
| 8,439,890 B2 | 5/2013 | Beyar |
| 8,556,813 B2 | 10/2013 | Cashman et al. |
| 8,574,247 B2 | 11/2013 | Adams et al. |
| 8,657,814 B2 | 2/2014 | Werneth |
| 8,709,075 B2 | 4/2014 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 8,986,339 B2 | 3/2015 | Warnack |
| 8,992,817 B2 | 3/2015 | Starnberg |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,131,949 B2 | 9/2015 | Coleman et al. |
| 9,138,249 B2 | 9/2015 | Adams et al. |
| 9,138,260 B2 | 9/2015 | Miller et al. |
| 9,180,280 B2 | 11/2015 | Hawkins et al. |
| 9,220,521 B2 | 12/2015 | Hawkins et al. |
| 9,237,984 B2 | 1/2016 | Hawkins et al. |
| 9,289,132 B2 | 3/2016 | Ghaffar et al. |
| 9,289,224 B2 | 3/2016 | Adams et al. |
| 9,320,530 B2 | 4/2016 | Grace |
| 9,333,000 B2 | 5/2016 | Hakala et al. |
| 9,375,223 B2 | 6/2016 | Wallace |
| 9,421,025 B2 | 8/2016 | Hawkins et al. |
| 9,433,428 B2 | 9/2016 | Hakala et al. |
| 9,504,809 B2 | 11/2016 | Bo |
| 9,510,887 B2 | 12/2016 | Burnett |
| 9,522,012 B2 | 12/2016 | Adams |
| 9,554,815 B2 | 1/2017 | Adams et al. |
| 9,555,267 B2 | 1/2017 | Ein-gal |
| 9,566,209 B2 | 2/2017 | Katragadda et al. |
| 9,579,114 B2 | 2/2017 | Mantell et al. |
| 9,629,567 B2 | 4/2017 | Porath et al. |
| 9,642,673 B2 | 5/2017 | Adams |
| 9,662,069 B2 | 5/2017 | De Graff et al. |
| 9,687,166 B2 | 6/2017 | Subramaniam |
| 9,730,715 B2 | 8/2017 | Adams |
| 9,764,142 B2 | 9/2017 | Imran |
| 9,814,476 B2 | 11/2017 | Adams et al. |
| 9,861,377 B2 | 1/2018 | Mantell et al. |
| 9,867,629 B2 | 1/2018 | Hawkins et al. |
| 9,894,756 B2 | 2/2018 | Weinkam et al. |
| 9,955,946 B2 | 5/2018 | Miller et al. |
| 9,974,963 B2 | 5/2018 | Imran |
| 9,974,970 B2 | 5/2018 | Nuta et al. |
| 9,993,292 B2 | 6/2018 | Adams et al. |
| 10,039,561 B2 | 8/2018 | Adams et al. |
| 10,136,829 B2 | 11/2018 | Deno et al. |
| 10,149,690 B2 | 12/2018 | Hawkins et al. |
| 10,159,505 B2 | 12/2018 | Hakala et al. |
| 10,194,994 B2 | 2/2019 | Deno et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,357,264 B2 | 7/2019 | Kat-Kuoy |
| 10,405,923 B2 | 9/2019 | Yu et al. |
| 10,406,031 B2 | 9/2019 | Thyzel |
| 10,420,569 B2 | 9/2019 | Adams |
| 10,441,300 B2 | 10/2019 | Hawkins |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,646,240 B2 | 5/2020 | Betelia et al. |

(56) References Cited

U.S. PATENT DOCUMENTS

| | | |
|---|---|---|
| 10,682,178 B2 | 6/2020 | Adams et al. |
| 10,702,293 B2 | 7/2020 | Adams et al. |
| 10,709,462 B2 | 7/2020 | Nguyen et al. |
| 10,758,255 B2 | 9/2020 | Adams |
| 10,842,567 B2 | 11/2020 | Grace et al. |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,076,874 B2 | 8/2021 | Hakala et al. |
| 11,213,661 B2 | 1/2022 | Spindler |
| 11,229,772 B2 | 1/2022 | Nita |
| 11,229,776 B2 | 1/2022 | Kugler et al. |
| 2001/0051784 A1 | 12/2001 | Brisken |
| 2002/0045811 A1 | 4/2002 | Kittrell et al. |
| 2002/0065512 A1 | 5/2002 | Fjield et al. |
| 2002/0082553 A1 | 6/2002 | Duchamp |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0176873 A1 | 9/2003 | Chernenko et al. |
| 2004/0002677 A1 | 1/2004 | Gentsler |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0243119 A1 | 12/2004 | Lane et al. |
| 2004/0249401 A1 | 12/2004 | Rabiner |
| 2005/0010095 A1 | 1/2005 | Stewart et al. |
| 2005/0021013 A1 | 1/2005 | Visuri |
| 2005/0080396 A1 | 4/2005 | Rental |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0299392 A1 | 12/2007 | Beyar et al. |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0195088 A1 | 8/2008 | Farr et al. |
| 2008/0214891 A1 | 9/2008 | Slenker et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0192495 A1 | 7/2009 | Ostrovsky et al. |
| 2009/0247945 A1 | 10/2009 | Levit |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160903 A1 | 6/2010 | Krespi |
| 2010/0168572 A1 | 7/2010 | Sliwa |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0245740 A1 | 10/2011 | Novak et al. |
| 2011/0257641 A1* | 10/2011 | Hastings ................ A61B 18/24 606/15 |
| 2011/0263921 A1 | 10/2011 | Vrba et al. |
| 2011/0275990 A1 | 11/2011 | Besser et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0157892 A1 | 6/2012 | Reitmajer et al. |
| 2012/0197245 A1 | 8/2012 | Burnett |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0116714 A1 | 5/2013 | Adams et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0345617 A1 | 12/2013 | Wallace |
| 2014/0005576 A1 | 1/2014 | Adams |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1* | 2/2014 | Hawkins ............... A61H 23/008 601/46 |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0180069 A1 | 6/2014 | Millett |
| 2014/0180126 A1 | 6/2014 | Millett |
| 2014/0180134 A1 | 6/2014 | Hoseit |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |

(56) References Cited

U.S. PATENT DOCUMENTS

| | | |
|---|---|---|
| 2014/0336632 A1 | 11/2014 | Toth |
| 2015/0005576 A1 | 1/2015 | Diodone et al. |
| 2015/0039002 A1 | 2/2015 | Hawkins |
| 2015/0073430 A1 | 3/2015 | Hakala et al. |
| 2015/0105715 A1 | 4/2015 | Pikus et al. |
| 2015/0119870 A1 | 4/2015 | Rudie |
| 2015/0141764 A1 | 5/2015 | Harks et al. |
| 2015/0276689 A1 | 10/2015 | Watanabe |
| 2015/0313732 A1 | 11/2015 | Fulton, III |
| 2015/0359432 A1 | 12/2015 | Ehrenreich |
| 2016/0008016 A1* | 1/2016 | Cioanta .............. A61B 18/245 601/4 |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0143522 A1 | 5/2016 | Ransbury |
| 2016/0183819 A1 | 6/2016 | Burnett |
| 2016/0183957 A1 | 6/2016 | Hakala et al. |
| 2016/0184022 A1 | 6/2016 | Grace et al. |
| 2016/0184023 A1 | 6/2016 | Grace et al. |
| 2016/0184570 A1 | 6/2016 | Grace et al. |
| 2016/0262784 A1 | 9/2016 | Grace et al. |
| 2016/0270806 A1 | 9/2016 | Wallace |
| 2016/0234534 A1 | 11/2016 | Hawkins et al. |
| 2016/0324564 A1* | 11/2016 | Gerlach .............. A61B 18/04 |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0056087 A1 | 3/2017 | Buckley |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0265942 A1* | 9/2017 | Grace .............. A61B 18/245 |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0049877 A1 | 2/2018 | Venkatasubramanian |
| 2018/0092763 A1 | 4/2018 | Dagan et al. |
| 2018/0098779 A1 | 4/2018 | Betelia et al. |
| 2018/0152568 A1 | 6/2018 | Kat-kuoy |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0104933 A1 | 4/2019 | Stern |
| 2019/0175111 A1 | 6/2019 | Genereux et al. |
| 2019/0175300 A1 | 6/2019 | Hom |
| 2019/0175372 A1 | 6/2019 | Boydan et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0282249 A1 | 9/2019 | Tran et al. |
| 2019/0282250 A1 | 9/2019 | Tran et al. |
| 2019/0328259 A1 | 10/2019 | Deno et al. |
| 2019/0388002 A1 | 12/2019 | Bozsak et al. |
| 2019/0388110 A1 | 12/2019 | Nguyen et al. |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0046949 A1 | 2/2020 | Chisena et al. |
| 2020/0054352 A1 | 2/2020 | Brouillette et al. |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0107960 A1 | 4/2020 | Bacher |
| 2020/0129195 A1 | 4/2020 | McGowan et al. |
| 2020/0129741 A1 | 4/2020 | Kawwas |
| 2020/0197019 A1 | 6/2020 | Harper |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0397453 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini et al. |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0128241 A1 | 5/2021 | Schultheis |
| 2021/0137598 A1 | 5/2021 | Cook |
| 2021/0153939 A1 | 5/2021 | Cook |
| 2021/0177445 A1 | 6/2021 | Nguyen |
| 2021/0186613 A1 | 6/2021 | Cook |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0307828 A1 | 10/2021 | Schultheis |
| 2021/0330384 A1 | 10/2021 | Cook |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0354578 A1 | 11/2022 | Cook |
| 2022/0387106 A1 | 12/2022 | Cook |
| 2023/0013920 A1 | 1/2023 | Massimini |

FOREIGN PATENT DOCUMENTS

| | | |
|---|---|---|
| CA | 2229806 | 3/1997 |
| CA | 2983655 | 10/2016 |
| CN | 102057422 | 5/2011 |
| CN | 109223100 | 1/2019 |
| CN | 110638501 A | 1/2020 |

(56) References Cited

FOREIGN PATENT DOCUMENTS

| | | |
|---|---|---|
| CN | 11399346 | 1/2022 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| DE | 3038445 A1 | 5/1982 |
| DE | 3836337 A | 4/1990 |
| DE | 3913027 A1 | 10/1990 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3318204 | 5/2018 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 4051154 | 9/2022 |
| GB | 1082397 | 9/1967 |
| JP | S62275446 A | 11/1987 |
| KR | 20050098932 | 10/2005 |
| KR | 20080040111 | 5/2008 |
| KR | 20160090877 A | 8/2016 |
| WO | WO9007904 A1 | 7/1990 |
| WO | WO9105332 A1 | 4/1991 |
| WO | 9203095 A1 | 3/1992 |
| WO | 1992008515 A2 | 5/1992 |
| WO | 9902095 A1 | 1/1999 |
| WO | 9920189 A1 | 4/1999 |
| WO | WO200067648 | 11/2000 |
| WO | WO2000067648 A1 | 11/2000 |
| WO | 2001003599 A1 | 1/2001 |
| WO | 2006006169 A2 | 1/2006 |
| WO | WO2009121017 | 10/2009 |
| WO | WO2009149321 A1 | 12/2009 |
| WO | 2010042653 A1 | 4/2010 |
| WO | WO2011094379 | 8/2011 |
| WO | 2011126580 A2 | 10/2011 |
| WO | WO2012025833 | 3/2012 |
| WO | WO20120052924 A1 | 4/2012 |
| WO | WO2012099974 A2 | 7/2012 |
| WO | WO20120120495 A2 | 9/2012 |
| WO | WO2013119662 | 8/2013 |
| WO | 20130169807 A1 | 11/2013 |
| WO | WO2014022436 A1 | 2/2014 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 2015177790 A1 | 11/2015 |
| WO | WO2016089683 A1 | 6/2016 |
| WO | WO2016090175 | 6/2016 |
| WO | 2016109739 | 7/2016 |
| WO | WO2016151595 A1 | 9/2016 |
| WO | WO2017004432 A1 | 1/2017 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 2018175322 | 9/2018 |
| WO | WO2019200201 A1 | 10/2019 |
| WO | WO2019215869 A1 | 11/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021067563 | 4/2021 |
| WO | 2021086571 A1 | 5/2021 |
| WO | 2021101766 A1 | 5/2021 |
| WO | WO2021096922 A1 | 5/2021 |
| WO | WO2021126762 A1 | 6/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021202248 A1 | 10/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | 2022055784 | 3/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022187058 | 9/2022 |
| WO | WO2022216488 | 10/2022 |
| WO | WO2022240674 | 11/2022 |
| WO | WO2022260932 | 12/2022 |

OTHER PUBLICATIONS

International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Search Report and Written Opinion dated Jul. 29, 2020 in PCT Application Serial No. PCT/US2020/034005.

(56) References Cited

OTHER PUBLICATIONS

International Search Report and Written Opinion, issued by the European Patent Office for PCT/2021/XXX, dated Sep. 30, 2021.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
Mcateer, James A., et al. "Ultracal-30 Gypsum Ailincial Stones for Research on the Mechinisms of Stone Breakage in Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 577-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PhD Thesis, 2009, Cranfield University.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies A Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'Nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologies, 2014, Pinnacle Biologies, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.
Hui, C., et al. "Research on sound fields generated by laser-induced liquid breakdown", Optica Applicata, 2010, pp. 898-907, vol. XL, No. 4, Xi'an, China.
Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

(56) References Cited

OTHER PUBLICATIONS

Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Vogel, A., et al. "Shock-Wave Energy and Acoustic Energy Dissipation After Laser-induced Breakdown", SPIE, 1998, pp. 180-189, vol. 3254, SPIE.
International Search Report and Written Opinion, issued by the EP/ISA, in PCT/US2021/048819, dated Jan. 14, 2022.
International Search Report and Written Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation. " 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery of Atrial Endocardial Potential Maps From Non-contact Electrode Data." Auckland Bioengineering Institute. (ID 1421).
Jiang et al., "Multielectrode Catheter for Substrate Mapping For Scar-related VT Ablation: A Comparison Between Grid Versus Linear Configurations." UChicago Medicine, Center for Arrhythmia Care, Chicago IL (ID 1368).
Sacher et al., "Comparison of Manual Vs Automatic Annotation To Identify Abnormal Substrate for Scar Related VT Ablation." LIRYC Institute, Bordeaux University Hospital, France (ID 1336).
International Search Report and Written Opinion dated Sep. 11, 2020 in PCT Application Serial No. PCT/US2020038517.
International Search Report and Written Opinion dated Sep. 9, 2020 in PCT Application Serial No. PCT/US2020038530.
International Search Report and Written Opinion dated Sep. 11, 2020 in PCT Application Serial No. PCT/US2020038521.
International Search Report and Written Opinion dated Sep. 7, 2020 in PCT Application Serial No. PCT/US2020034642.
International Preliminary Report on Patentability dated Sep. 15, 2020 in PCT Application Serial No. PCT/US2019/022009.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.

Poduval, R., et al. "Optical fiber ultrasound transmitter with electrospun carbon nanotube-polymer composite", Appl. Phys. Lett, 2017, vol. 110, 223701, American Institute of Physics.
Tian, J., et al. "Distributed fiber-optic laser-ultrasound generation based on ghost-mode of tilted fiber Bragg gratings", Dptics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, dated Jan. 16, 2019.
European Search Report, for European Patent Application No. 18185152.8, dated Dec. 20, 2018.
Provisional International Search Report and Written Opinion dated Feb. 19, 2021 in PCT Application Serial No. PCT/US2020/059960.
Nademanee, Koonlawee, et al. "A new approach for catheter ablation of atrial fibrillation: mapping of the alectrophysiologic substrate." Journal of the American College of Cardiology 43.11 (2004): 2044-2053.
Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.

(56) References Cited

OTHER PUBLICATIONS

Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced ShockWave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, dated Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Schafter+Kirchhoff, Laser Beam Couplers series 60SMS for coupling into single-mode and polarization-maintaining fiber cables, Schafter+Kirchhoff, pp. 1-5, Germany.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/ US2022/015577.
International Search Report and Written Opinion dated May 13, 2022 in PCT Application Serial No. PCT/US2022/017562.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Inti avascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and ShockWaves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation an kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.
Costanzo, F., "Underwater Explosion Phenomena and Shock Physics", Research Gate, 2011.

(56) References Cited

OTHER PUBLICATIONS

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.
De Silva, K., et al. "A Calcific, Undilatable Stenosis Lithoplasty, a New Tool in the Box?", JACC: Cardiovascular Interventions, 2017, vol. 10, No. 3, Elsevier.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Hutchens, Thomas C., et al. "Detachable fiber optic tips for use in thulium fiber laser lithotripsy", Journal of Biomedical Optics, Mar. 2013, vol. 18(3), SPIE.
Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.
Kristiansen, M., et al. "High Voltage Water Breakdown Studies", DoD, 1998, Alexandria, VA, USA.
Dwyer, J. R., et al. "A study of X-ray emission from laboratory sparks in air at atmospheric pressure", Journal of Geophysical Research, 2008, vol. 113, American Geophysical Union.
Jansen, Duco E., et al. "Effect of Pulse Duration on Bubble Formation and Laser-Induced Pressure Waves During Holmium Laser Ablation", Lasers in Surgery and Medicine 18,1996, pp. 278-293, Wiley-Liss Inc., Austin, TX, USA.
Shangguan, HanQun et al. "Effects of Material Properties on Laser-induced Bubble Formation in Absorbing Liquids and on Submerged Targets", SPIE, 1997, pp. 783-791, vol. 2869.
Varghese, B., et al. "Effects of polarization and absorption on laser induced optical breakdown threshold for skin rejuvenation", SPIE, Mar. 9, 2016, vol. 9740, SPIE, San Francisco, USA.
Varghese, B., et al. "Effects of polarization and apodization on laser induced optical breakdown threshold", Optics Express, Jul. 29, 2013, vol. 21, No. 15, Optical Society of America.
Bonito, Valentina, "Effects of polarization, plasma and thermal initiation pathway on irradiance threshold of laser induced optical breakdown", Philips Research, 2013, The Netherlands.
Vogel, A. et al. "Energy balance of optical breakdown in water at nanosecond to femtosecond time scales", Applied Physics B 68, 1999, pp. 271-280, Springer-Verlag.
Kang, Hyun W., et al. "Enhanced photocoagulation with catheter based diffusing optical device", Journal of Biomedical Optics, Nov. 2012, vol. 17(11), SPIE.
Esch, E., et al. "A Simple Method for Fabricating Artificial Kidney Stones of Different Physical Properties", National Institute of Health Public Access Author Manuscript, Aug. 2010.
Isner, Jeffrey M., et al. "Excimer Laser Atherectomy", Circulation, Jun. 1990, vol. 81, No. 6, American Heart Association, Dallas, TX, USA.
Israel, Douglas H., et al. "Excimer Laser-Facilitated Balloon Angioplasty of a Nondilateable Lesion", JACC, Oct. 1991, vol. 18, No. 4, American College of Cardiology, New York, USA.
Van Leeuwen, Ton G., et al. "Excimer Laser Induced Bubble: Dimensions,Theory, and Implications for Laser Angioplasty", Lasers in Surgery and Medicine 18, 1996, pp. 381-390, Wiley-Liss Inc., Utrecht, The Netherlands.
Nguyen, H., et al. "Fabrication of multipoint side-firing optical fiber by laser micro-ablation", Optics Letters, May 1, 2017, vol. 42, No. 9, Optical Society of America.
Zheng, W., "Optic Lenses Manufactured on Fiber Ends", 2015, IEEE, Duncan, SC, USA.
Whitesides, George M., et al. "Fluidic Optics", 2006, vol. 6329, SPIE, Cambridge, MA, USA.
Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.
Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, p. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
International Search Report and Written Opinion dated Aug. 25, 2022 in PCT Application Serial No. PCT US/2022/028035.
International Search Report and Written Opinion dated Sep. 15, 2022 in PCT Application Serial No. PCT US/2022/032045.
International Search Report and Written Opinion dated Nov. 8, 2022 in PCT Application Serial No. PCT US/2022/039678.
International Search Report and Written Opinion, PCT Application Serial No. PCT/US2022/047751 dated Feb. 10, 2023, by the European Patent Office.
International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
Medlight, "Cylindrical light diffuser Model RD-ML", Medlight S.A., Switzerland. 2015. (This reference was cited in a prior Information Disclosure Statement. However, the relevant date was missing. The date has now been added.).
Medlight, "Cylindircal light diffuser Model RD", Medlight S.A., Switzerland. 2015. (This reference was cited in a prior Information Disclosure Statement. However, the relevant date was missing. The date has now been added.).
Ohl, Siew-Wan, et al. "Bubbles with shock waves and ultrasound: a review", Interface Focus, pp. 1-15, vol. 5, The Royal Society Publishing Oct. 2015. (This reference was cited in a prior Information Disclosure Statement. However, the relevant date was missing. The date has now been added.).
Schafter+Kirchhoff, Laser Beam Couplers series 60SMS for coupling into single-mode and polarization-maintaining fiber cables, Schafter+Kirchhoff, pp. 1-5, Germany. Dec. 2, 2021. (This reference was cited in a prior Information Disclosure Statement. However, the relevant date was missing. The date has now been added.).
Meng et al., "Accurate Recovery of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).
Jiang et al., "Multielectrode Catheter for Substrate Mapping for Scar-related VT Ablation: A Comparison Between Grid Versus Linear Configurations." UChicago Medicine, Center for Anrhythmia Care, Chicago IL (Id 1368). Posterior conference in San Francisco, May 8-11, 2019. (This reference was cited in a prior Information Disclosure Statement. However, the relevant date was missing. The date has now been added.).
Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019. (This reference

(56) References Cited

OTHER PUBLICATIONS was cited in a prior Information Disclosure Statement. However, the relevant date was missing. The date has now been added.).

* cited by examiner

SUPERHEATING SYSTEM FOR INERTIAL IMPULSE GENERATION TO DISRUPT VASCULAR LESIONS

RELATED APPLICATIONS

This application claims priority on U.S. Provisional Application Ser. No. 62/865,507, filed on Jun. 24, 2019, and entitled "SUPERHEATING SYSTEM FOR INERTIAL IMPULSE GENERATION TO DISRUPT VASCULAR LESIONS", and on U.S. Provisional Application Ser. No. 62/865,524, filed on Jun. 24, 2019, and entitled "RESISTIVE HEATER SUPERHEATING SYSTEM FOR INERTIAL IMPULSE GENERATION TO DISRUPT VASCULAR LESIONS". To the extent permitted, the contents of U.S. Provisional Application Ser. Nos. 62/865,507 and 62/865,524 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

In a first aspect, a catheter system for imparting pressure to induce fractures in a vascular lesion within or adjacent a vessel wall is included. The catheter system includes a catheter configured to advance to the vascular lesion located within a blood vessel. The catheter can include an elongate shaft and a balloon coupled to the elongate shaft. The balloon can include a balloon wall and be configured to expand from a collapsed configuration suitable for advancing the catheter through a patient's vasculature to a first expanded configuration suitable for anchoring the catheter in position relative to a treatment site. The catheter system can include a superheating system configured to heat a balloon fluid within the balloon rapidly enough to achieve spontaneous vaporization of the balloon fluid and generate inertial bubbles and acoustic pressure waves.

In a second aspect, in addition to one or more of the preceding or following aspects, or in the alternative to some aspects, where the superheating system includes a first light guide extending along the elongate shaft and configured to be placed in optical communication with a light source at a proximal portion of the first light guide, the first light guide defining a first light window at a distal portion of the light guide.

In a third aspect, in addition to one or more of the preceding or following aspects, or in the alternative to some aspects, where the first light guide is an optical fiber and where the light source is a laser.

In a fourth aspect, in addition to one or more of the preceding or following aspects, or in the alternative to some aspects, where the catheter system can further include a second light guide coupled to the elongate shaft, where the second light guide is in optical communication with the light source.

In a fifth aspect, in addition to one or more of the preceding or following aspects, or in the alternative to some aspects, where the first light guide includes a spiral path around a distal portion of the elongate shaft.

In a sixth aspect, in addition to one or more of the preceding or following aspects, or in the alternative to some aspects, where the distal portion of the light guide includes a diverting feature configured to direct light in the light guide toward a side surface portion of the distal portion of the light guide, and where the diverting feature is selected from a group including of a reflecting element and a refracting element; and a first light window positioned on the side surface portion.

In a seventh aspect, in addition to one or more of the preceding or following aspects, or in the alternative to some aspects, where the light guide includes a first fiber diffuser in a distal portion of the light guide, and where the first fiber diffuser directs light from the light guide to exit the light guide at a side surface portion of the light guide, and where the side surface portion is in optical communication with a first light window.

In an eighth aspect, in addition to one or more of the preceding or following aspects, or in the alternative to some aspects, where the first fiber diffuser is selected from a group including of a machined portion of the light guide, a laser-machined portion of the light guide, fiber Bragg gratings, a fused splicing forming at least one internal mirror, and a splicing of two or more diffuse regions.

In a ninth aspect, in addition to one or more of the preceding or following aspects, or in the alternative to some aspects, where the catheter system can further include a plurality of light windows including the first light window, and a plurality of fiber diffusers in the distal portion of the light guide including the first fiber diffuser, where each fiber diffuser directs light from the light guide to exit the light guide at a side surface portion of the light guide, and where each side surface portion is in optical communication with one of the plurality of light windows.

In a tenth aspect, in addition to one or more of the preceding or following aspects, or in the alternative to some aspects, where the plurality of light windows is axially spaced apart with at least one intervening non-emitting portion of the light guide disposed between each of the plurality of light windows.

In an eleventh aspect, in addition to one or more of the preceding or following aspects, or in the alternative to some aspects, where the side surface portion is a cylindrical side surface portion and the first light window is configured as a cylindrical window.

In a twelfth aspect, in addition to one or more of the preceding or following aspects, or in the alternative to some aspects, where the first light window is in optical communication with the balloon fluid.

In a thirteenth aspect, in addition to one or more of the preceding or following aspects, or in the alternative to some aspects, where the catheter system can further include a thermally conductive photonic absorption layer disposed on the first light window and configured to be in optical communication with the light source, where the thermally conductive photonic absorption layer is configured to absorb a photonic energy from the light guide and convert the photonic energy into thermal energy to achieve spontaneous vaporization of a balloon fluid within the balloon and to generate inertial bubbles and acoustic pressure waves.

In a fourteenth aspect, in addition to one or more of the preceding or following aspects, or in the alternative to some aspects, where the elongate shaft defines a guidewire lumen.

In a fifteenth aspect, in addition to one or more of the preceding or following aspects, or in the alternative to some aspects, where the elongate shaft defines an inflation lumen surrounding the guidewire lumen, and where the inflation lumen is in fluid communication with the balloon at a distal portion of the elongate shaft.

In a sixteenth aspect, a method for generating pressure to induce fractures in a vascular lesion within or adjacent a vessel wall of a blood vessel is included. The method can include advancing a catheter to a vascular lesion location within the blood vessel, where the catheter can include a balloon coupled to an elongate shaft. The method can include expanding the balloon from a collapsed configuration suitable for advancing the catheter through a patient's vasculature to a first expanded configuration suitable for anchoring the catheter in position relative to the vascular lesion location. The method can include after expanding the balloon, heating a balloon fluid in contact with a superheating system to achieve spontaneous vaporization of the balloon fluid and generation of inertial bubbles and acoustic pressure waves directed toward a balloon wall, thereby imparting pressure upon the vascular lesion to induce fractures in the vascular lesion.

In a seventeenth aspect, in addition to one or more of the preceding or following aspects, or in the alternative to some aspects, where heating the balloon fluid includes heating the balloon fluid to above its boiling point in more than 1 nanosecond and less than 10 seconds.

In an eighteenth aspect, a catheter system for imparting pressure to induce fractures in a vascular lesion within or adjacent a vessel wall is included. The catheter system can include a catheter configured to advance to the vascular lesion located within a blood vessel, where the catheter can include an elongate shaft and a balloon coupled to the elongate shaft. The balloon includes a balloon wall and is configured to expand from a collapsed configuration suitable for advancing the catheter through a patient's vasculature to a first expanded configuration suitable for anchoring the catheter in position relative to a treatment site. The catheter system can include a superheating system configured to heat a balloon fluid within the balloon rapidly enough to achieve spontaneous vaporization of the balloon fluid and generate inertial bubbles and acoustic pressure waves, where the superheating system includes a first light guide extending along the elongate shaft and configured to be placed in optical communication with a light source at a proximal portion of the first light guide, and where the first light guide includes at least a first light window in optical communication with a distal portion of the light guide. The first light guide can be an optical fiber and where the light source is a laser.

In a nineteenth aspect, in addition to one or more of the preceding or following aspects, or in the alternative to some aspects, the catheter system can further include a thermally conductive photonic absorption layer in optical communication with the first light window and the light source, where the thermally conductive photonic absorption layer is configured to absorb a photonic energy from the light guide and convert the photonic energy into thermal energy to achieve spontaneous vaporization of a balloon fluid within the balloon and to generate inertial bubbles and acoustic pressure waves.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DESCRIPTION

Treatment of vascular lesions can reduce major adverse events or death in affected subjects. A major adverse event is one that can occur anywhere within the body due to the presence of a vascular lesion. Major adverse events can include, but are not limited to major adverse cardiac events, major adverse events in the peripheral or central vasculature, major adverse events in the brain, major adverse events in the musculature, or major adverse events in any of the internal organs.

Various catheter systems for imparting pressure to induce fractures in a vascular lesion within or adjacent a vessel wall are described. The catheter systems can include a catheter configured to advance to the vascular lesion located within a blood vessel, the catheter including an elongate shaft and a balloon coupled to the elongate shaft. The catheter systems can include a balloon that includes a balloon wall and is configured to expand from a collapsed configuration suitable for advancing the catheter through a patient's vasculature to a first expanded configuration suitable for anchoring the catheter in position relative to a treatment site. The catheter systems herein can include a superheating system configured to heat a balloon fluid within the balloon rapidly enough to achieve spontaneous vaporization of the balloon fluid and generate inertial bubbles and acoustic pressure waves.

Figure 1:
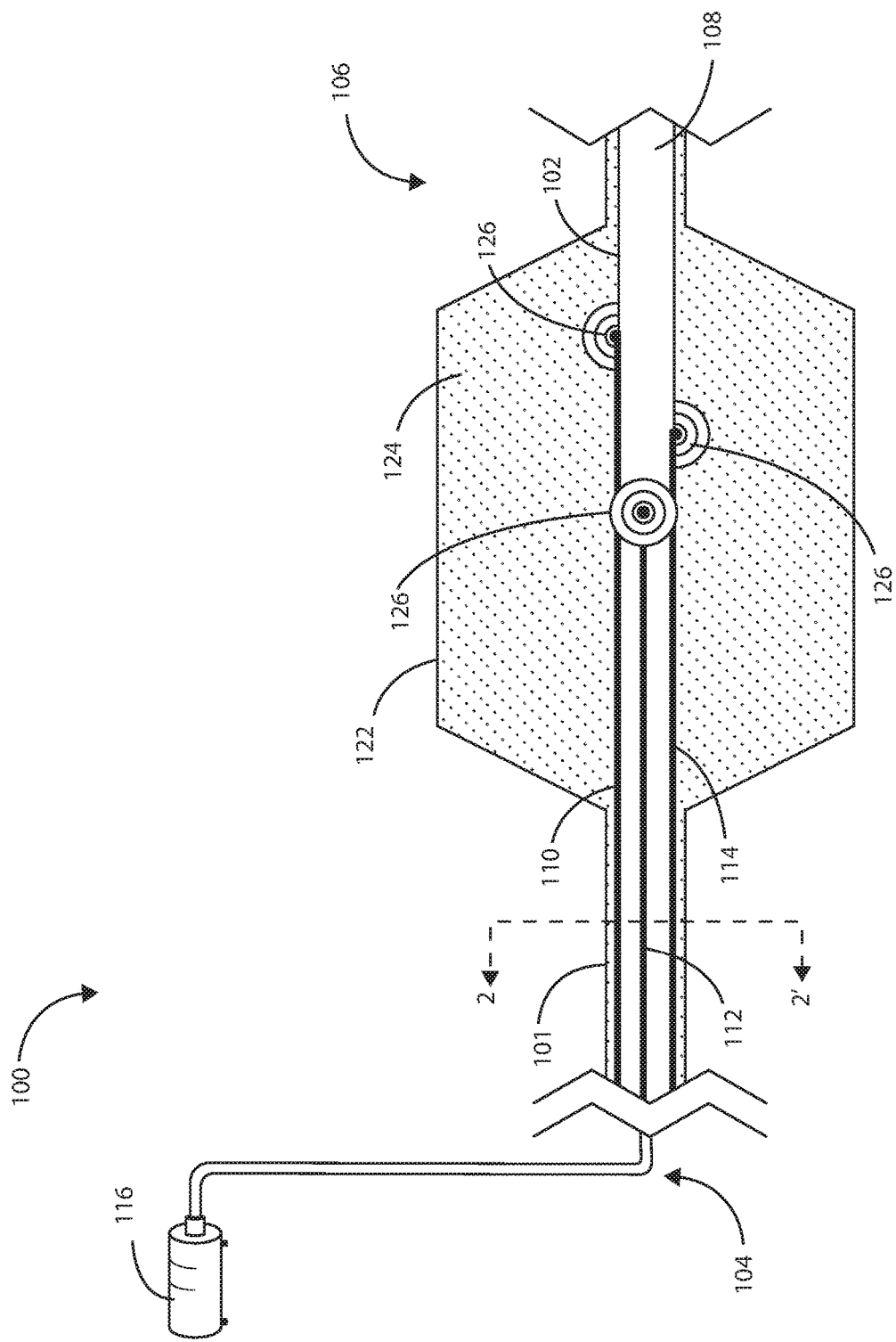
FIG. 1 is a schematic longitudinal cross-sectional view of a catheter in accordance with various embodiments herein.

It will be appreciated that the catheters herein can include many different forms. Referring now to FIG. 1, a schematic cross-sectional view of a catheter system 100 is shown in accordance with various embodiments herein. Catheter system 100 is suitable for imparting pressure to induce fractures in a vascular lesion within or adjacent a vessel wall. Catheter system 100 includes a catheter 101. Catheter 101 can be configured to advance to a vascular lesion location within or adjacent a blood vessel. In some embodiments, the vascular lesion can include a calcified vascular lesion. In some embodiments, the vascular lesion can include a fibrous vascular lesion. The catheter 101 can include an elongate shaft 102 and a balloon 122 coupled to the elongate shaft 102. The elongate shaft 102 can extend from a proximal portion 104 to a distal portion 106, and can also include a lumen 108. In some embodiments, lumen 108 includes a guidewire lumen. The elongate shaft 102 can further include an inflation lumen, as will be discussed in more detail below. In some embodiments, the catheter 101 can have a distal portion opening and can accommodate and be tracked over a guidewire to a treatment location. In some embodiments, the catheter 101 does not include a lumen. In embodiments where the elongate shaft 102 does not include a lumen to be accessed by a caregiver, the elongate shaft 102 can be configured to allow the catheter to be steered through a patient's vasculature.

The elongate shaft 102 of catheter 101 can be coupled to a first light guide 110 in optical communication with a light source 116. In some embodiments, the first light guide 110 can be an optical fiber and the light source can be a laser. The light source 116 can be in optical communication with the first light guide 110 at a proximal portion 104 of the elongate shaft 102. In some embodiments, the elongate shaft can be coupled to multiple light guides such as a second light guide 112 and a third light guide 114. The light source 116 can be in optical communication with the second light guide 112 and the third light guide 114 at a proximal portion 104 of the elongate shaft 102.

It will be appreciated that the catheters herein can include any number of light guides in optical communication with the light source 116 at the proximal portion 104 and the balloon fluid 124 at the distal portion 106. For example, in some embodiments, the catheters herein can include from one light guide to five light guides. In other embodiments, the catheters herein can include from five light guides to fifteen light guides. In yet other embodiments, the catheters herein can include from ten light guides to thirty light guides. The catheters herein can include one, two, three, four, five, six, seven, eight, nine, or ten light guides. The catheters can include 11, 12, 13, 14, 15, 16, 17, 18, 19, 20, 21, 22, 23, 24, 25, 26, 27, 28, 29, or 30 light guides. It will be appreciated that catheters herein can include any number of light guides that can fall within a range, wherein any of the forgoing numbers can serve as the lower or upper bound of the range, provided that the lower bound of the range is a value less than the upper bound of the range. In some embodiments, the catheters herein can include more than 30 light guides.

The balloon 122 of catheter 101 can include a balloon wall and can expand from a collapsed configuration suitable for advancing the catheter through a patient's vasculature to a first expanded configuration suitable for anchoring the catheter in position relative to a treatment site. Expansion of the balloons herein to various expanded configurations will be discussed in more detail below. The catheter system 100 can further include a superheating system configured to heat a balloon fluid 124 within the balloon 122 rapidly enough to achieve spontaneous vaporization of the balloon fluid 124 and generate inertial bubbles 126 and acoustic pressure waves. The superheating system can include a first light guide 110 extending along the elongate shaft 102 and configured to be placed in optical communication with a light source 116 at a proximal portion 104 of the first light guide 110. The first light guide 110 can be in optical communication with the balloon fluid 124 at a distal portion 106 of the first light guide 110. The first light guide 110 can include at least a first light window (not shown) in optical communication with a distal portion 106 of the first light guide 110.

The light guides herein can include a plurality of light windows, including a first light window, along the length of a light guide and disposed within the balloon 122. For example, in some embodiments, each light guide herein can include from one light window to five light windows. In other embodiments, each light guide herein can include from five light windows to fifteen light windows. In yet other embodiments, each light guide herein can include from ten light windows to thirty light windows. Each light guide herein can include one, two, three, four, five, six, seven, eight, nine, or ten light windows. Each light guide herein can include 11, 12, 13, 14, 15, 16, 17, 18, 19, 20, 21, 22, 23, 24, 25, 26, 27, 28, 29, or 30 light windows. It will be appreciated that light guides herein can include any number of light windows that can fall within a range, wherein any of the forgoing numbers can serve as the lower or upper bound of the range, provided that the lower bound of the range is a value less than the upper bound of the range. In some embodiments, the light guides herein can include more than 30 light windows.

The light windows can be disposed along the length of each light guide in various configurations and spacings. The light windows can be longitudinally separated from each other along the length of a light guide by a distance of from zero millimeters (mm) to 500 mm. In some embodiments, the light windows can be longitudinally separated from each other along the length of a light guide by a distance of from 0 mm to 300 mm. In some embodiments, the longitudinal separation between the light windows can be greater than or equal to 0 mm, 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, or 300 mm, or can be an amount falling within a range between any of the foregoing. The light windows can be staggered along one or more light guides in a proximal to distal fashion and can be staggered both longitudinally and circumferentially. In some embodiments, the light windows can be disposed along a light guide in a spiral path around a distal portion of the elongate shaft.

When multiple light windows are present, the light windows can be radially offset from one another by about at least about or about 45 degrees. In some embodiments, the light windows can be radially offset from one another by at least about or about 60 degrees. In some embodiments, the light windows can be axially offset from one another by about or at least about 90 degrees. In some embodiments, the light windows can be radially offset from one another by at most about or about 180 degrees. In some embodiments, a plurality of light windows will be evenly spaced and radially offset from each other so that where there are n light windows, they are spaced apart by 360 degrees divided by n. In some embodiments, the light windows are not evenly spaced apart but are concentrated in one region of the elongate shaft in an asymmetrical fashion.

Figure 2:
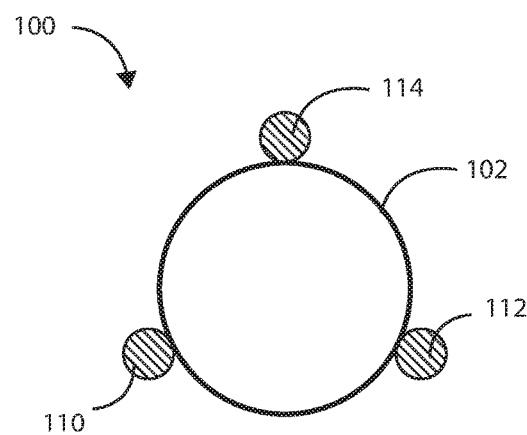
FIG. 2 is a schematic axial cross-sectional view of an elongate shaft of a catheter along line 2-2' in FIG. 1 in accordance with various embodiments herein.
Figure 3:
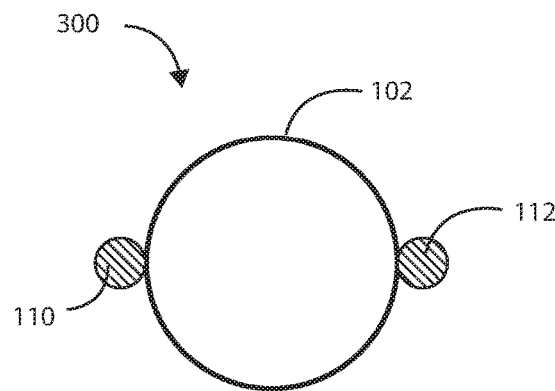
FIGS. 3-5 are schematic axial cross-sectional views of additional configurations for an elongate shaft of the catheter along line 2-2' in FIG. 1 in accordance with various embodiments herein.
Figure 4:
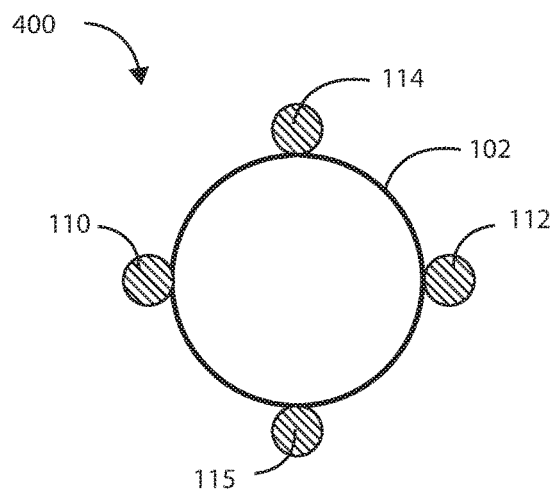
Figure 5:
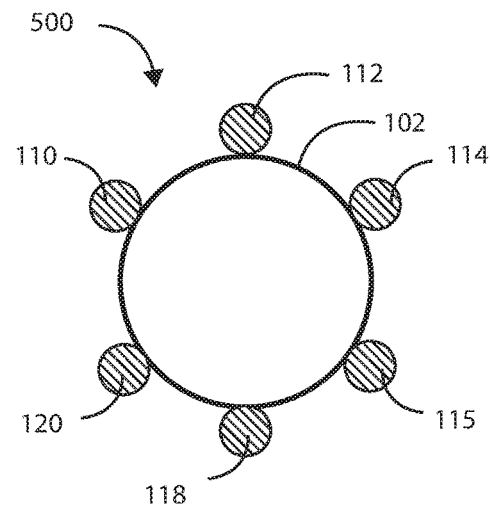

Examples of catheters having multiple light guides disposed about an elongate shaft at different positions around the circumference are shown in FIGS. 2-5. Referring now to FIG. 2, a schematic cross-sectional view of a catheter 101 of FIG. 1 along line 2-2' in FIG. 1 is shown in accordance with various embodiments herein. Catheter 101 includes an elongate shaft 102, a first light guide 110, a second light guide 112, and a third light guide 114 separated by about 120 degrees around the circumference. Referring now to FIGS. 3-5 schematic cross-sectional views of additional configurations for catheters having multiple light guides are shown in accordance with various embodiments herein. The configuration of catheter 300 in FIG. 3 includes an elongate shaft 102, a first light guide 110, and a second light guide 112 separated by about 180 degrees around the circumference. The configuration of catheter 400 in FIG. 4 includes an elongate shaft 102, a first light guide 110, a second light guide 112, a third light guide 114, and a fourth light guide 115 separated by about 90 degrees around the circumference. The configuration of catheter 500 shown in FIG. 5 includes an elongate shaft 102, a first light guide 110, a second light guide 112, a third light guide 114, a fourth light guide 115, a fifth light guide 118, and a sixth light guide 120 separated by about 60 degrees around the circumference.

When multiple light guides are present, the light guides can be radially offset from one another by at least about or about 45 degrees. In some embodiments, the light guides can be radially offset from one another by at least about or about 60 degrees. In some embodiments, the light guides can be radially offset from one another by about or at least about 90 degrees. In some embodiments, the light guides can be radially offset from one another by at most about or about 180 degrees. In some embodiments, a plurality of light guides will be evenly spaced and radially offset from each other so that where there are n light guides, they are spaced apart by 360 degrees divided by n. In other embodiments, the light guides will be unevenly spaced and radially offset from each other. In some embodiments, each of the light guide locations shown in FIGS. 2-5 or otherwise described herein include two parallel light guides that are touching.

Figure 6:
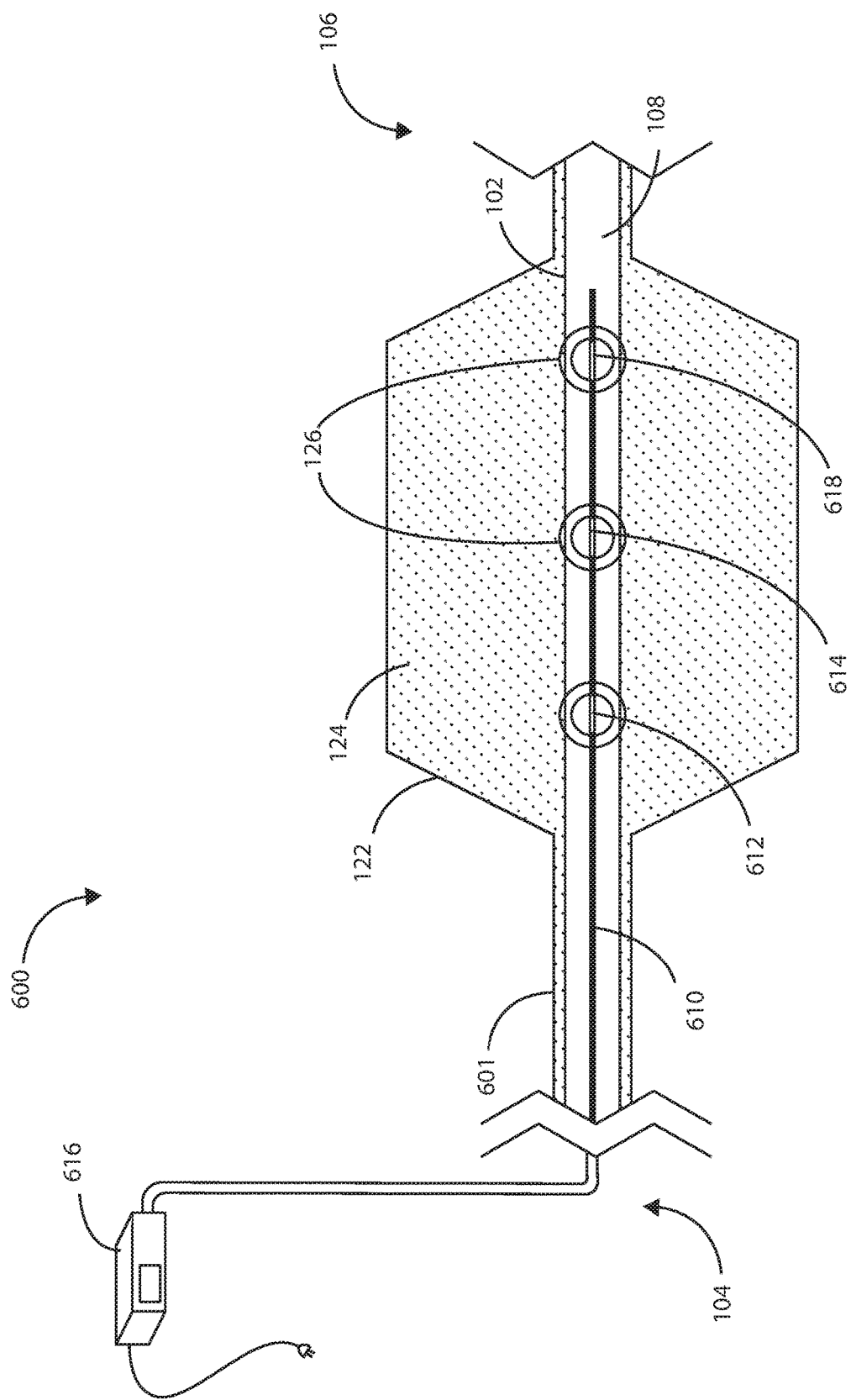
FIG. 6 is a schematic longitudinal cross-sectional view of a catheter in accordance with various embodiments herein.

Catheter Embodiments Using Electric Energy Source (FIG. 6)

The catheter systems herein can also include catheters that include electrical leads for powering one or more resistive heaters to cause superheating of the balloon fluid. Referring now to FIG. 6, a schematic cross-sectional view of an additional embodiment of a catheter system 600 is shown in accordance with various embodiments herein. Catheter system 600 is suitable for imparting pressure to induce fractures in a vascular lesion within or adjacent a vessel wall. Catheter system 600 includes a catheter 601. Catheter 601 can be configured to advance to a vascular lesion location within or adjacent a blood vessel. In some embodiments, the vascular lesion can include a calcified vascular lesion. The catheter 601 can include an elongate shaft 102 and a balloon 122 coupled to the elongate shaft 102. The elongate shaft 102 can extend from a proximal portion 104 to a distal portion 106, and can also include a lumen 108. In some embodiments, lumen 108 is a guidewire lumen. The elongate shaft 102 can further include an inflation lumen, as will be discussed in more detail below. In some embodiments, the catheter 601 can define a distal end opening at its distal end and can accommodate and be tracked over a guidewire to a treatment location. In some embodiments, the catheter 601 does not include a guidewire lumen. In embodiments where the elongate shaft 102 does not include a guidewire lumen, the elongate shaft 102 can be configured to allow the catheter to be steered through a patient's vasculature, such as by having a tip that aids maneuverability.

The elongate shaft 102 of catheter 601 can enclose or be coupled to a first electrical lead 610 in electrical communication with a generator 616 of a voltage potential. The generator 616 can be in electrically connected to the first electrical lead 610 at a proximal portion 104 of the elongate shaft 102. In some embodiments, the elongate shaft can enclose or be coupled to multiple electrical leads such as a second electrical lead and a third electrical lead (first and second electrical leads are not shown in FIG. 6). The generator 616 can be electrically connected to the second electrical lead and the third electrical lead at a proximal portion 104 of the elongate shaft 102.

It will be appreciated that the catheters herein can include any number of electrical leads in electrical communication with the generator 616 at the proximal portion 104 and the balloon fluid 124 at the distal portion 106. In some embodiments, each electrical lead is connected to a separate resistive heater. For example, in some embodiments, the catheters herein can include from one electrical lead to five electrical leads. In other embodiments, the catheters herein can include from five electrical leads to fifteen electrical leads. In yet other embodiments, the catheters herein can include from ten electrical leads to thirty electrical leads. The catheters herein can include one, two, three, four, five, six, seven, eight, nine, or ten electrical leads. The catheters can include 11, 12, 13, 14, 15, 16, 17, 18, 19, 20, 21, 22, 23, 24, 25, 26, 27, 28, 29, or 30 electrical leads. It will be appreciated that catheters herein can include any number of electrical leads that can fall within a range, wherein any of the forgoing numbers can serve as the lower or upper bound of the range, provided that the lower bound of the range is a value less than the upper bound of the range. In some embodiments, the catheters herein can include more than 30 electrical leads.

The balloon 122 of catheter system 600 can include a balloon wall and can expand from a collapsed configuration suitable for advancing the catheter through a patient's vasculature to a first expanded configuration suitable for anchoring the catheter in position relative to a treatment site. Expansion of the balloons herein to various expanded configurations will be discussed in more detail below. The catheter system 600 can further include a superheating system configured to heat a balloon fluid 124 within the balloon 122 rapidly enough to achieve spontaneous vaporization of the balloon fluid 124 and generate inertial bubbles 126 and acoustic pressure waves. The superheating system can include a first electrical lead 610 extending along the elongate shaft 102 and configured to be placed in electrical communication with a generator 616 of a voltage potential at a proximal portion 104 of the first electrical lead 610. The first electrical lead 610 can be in electrical communication with the balloon fluid 124 at a distal portion 106 of the first electrical lead 610.

The first electrical lead 610 can include at least a first resistive heating element 612 in electrical communication with a distal portion 106 of the first electrical lead 610. The first resistive heating element 612 can be in thermal communication with the balloon fluid 124 at a distal portion 106 of the first electrical lead 610. In some embodiments, the first electrical lead 610 can include a second resistive heating element 614 at the distal portion of the first electrical lead. The first electrical lead 610 can be in electrical communication with the second resistive heating element 614, where the second resistive heating element 614 is in thermal communication with the balloon fluid 124 at a distal portion 106 of the first electrical lead 610. The first resistive heating element 612 and the second resistive heating element 614 can be axially spaced from each other along the elongate shaft 102. The first electrical lead 610 can be in electrical communication with a third resistive heating element 618, where the third resistive heating element 618 can be in thermal communication with the balloon fluid 124 at a distal portion 106 of the first electrical lead 610.

The electrical leads herein can be in electrical communication with a plurality of resistive heating elements, including a first resistive heating element, along the length of an electrical lead and disposed within the balloon 122. For example, in some embodiments, each electrical lead herein can include from one resistive heating element to five resistive heating elements. In other embodiments, each electrical lead herein can include from five resistive heating elements to fifteen resistive heating elements. In yet other embodiments, each electrical lead herein can include from ten resistive heating elements to thirty resistive heating elements. Each electrical lead herein can include one, two, three, four, five, six, seven, eight, nine, or ten resistive heating elements. Each electrical lead herein can include 11, 12, 13, 14, 15, 16, 17, 18, 19, 20, 21, 22, 23, 24, 25, 26, 27, 28, 29, or 30 resistive heating elements. It will be appreciated that electrical leads herein can include any number of resistive heating elements that can fall within a range, wherein any of the forgoing numbers can serve as the lower or upper bound of the range, provided that the lower bound of the range is a value less than the upper bound of the range. In some embodiments, the light guides herein can include more than 30 resistive heating elements. When multiple electrical leads are present, the electrical leads can be disposed about the elongate shaft in various positions. It will be appreciated that while the embodiments shown in FIGS. 2-5 are described as depicting an elongate shaft having one or more light guides disposed about the elongate shaft, the electrical leads described herein can also be disposed about the elongate shaft in the same location configurations as the light guides shown and described with respect to FIGS. 2-5.

The resistive heating elements can be disposed along the length of an electrical lead in various configurations and spacings. The resistive heating elements can be disposed along the length of the elongate shaft and each be connected to separate electrical leads in various configurations and spacings. The resistive heating elements can be longitudinally separated from each other along the length of an electrical lead or the elongate shaft by a distance of from zero millimeters (mm) to 500 mm. In some embodiments, the resistive heating elements can be longitudinally separated from each other along the length of an electrical lead or the elongate shaft by a distance of from 0 mm to 300 mm. In some embodiments, the longitudinal separation between the resistive heating elements can be greater than or equal to 0 mm, 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, or 300 mm, or can be an amount falling within a range between any of the foregoing. The resistive heating elements can be staggered along the elongate shaft using one or more electrical leads in a proximal to distal fashion and can be staggered both longitudinally and circumferentially. In some embodiments, the resistive heating elements can be disposed in a spiral path around a distal portion of the elongate shaft.

When multiple resistive heating elements are present, the resistive heating elements can be radially offset from one another by about at least about or about 45 degrees. In some embodiments, the resistive heating elements can be radially offset from one another by at least about or about 60 degrees. In some embodiments, the resistive heating elements can be radially offset from one another by about or at least about 90 degrees. In some embodiments, the resistive heating elements can be radially offset from one another by at most about or about 180 degrees. In some embodiments, a plurality of resistive heating elements will be evenly spaced and radially offset from each other so that where there are n resistive heating elements, they are spaced apart by 360 degrees divided by n. In some embodiments, the resistive heating elements are not evenly spaced apart but are concentrated in one region of the elongate shaft in an asymmetrical fashion.

In some embodiments, catheter system for imparting pressure to induce fractures in a vascular lesion within or adjacent a vessel wall can include a catheter configured to advance to a lesion location within the blood vessel. The catheter can include an elongate shaft and a balloon coupled to the elongate shaft, and a first electrical lead extending along the elongate shaft and configured to be placed in electrical communication with, or electrically connected to, a voltage potential at a proximal portion of the first electrical lead. The first electrical lead can be electrically connected to a resistive heating element at a distal portion of the first electrical lead, where the resistive heating element is in thermal communication with the balloon fluid. The balloon can include a balloon wall and can be configured to expand from a collapsed configuration suitable for advancing the catheter through a patient's vasculature to a first expanded configuration suitable for anchoring the catheter in position relative to a treatment site. The catheter system can include a superheating system configured to heat a balloon fluid within the balloon rapidly enough to achieve spontaneous vaporization of the balloon fluid and generate inertial bubbles and acoustic pressure waves. The catheter system can be configured to fill the balloon with fluid.

Suitable resistive heating elements can include hot filament elements, such as a low voltage electric heater or microheater elements. In some embodiments, the microheater elements can be a thin microfilm heater. The resistive heating elements described herein can be made from materials that, include, but are not to be limited to those made from tungsten, aluminum, brass, carbon, copper, palladium, titanium, platinum, tantalum, tantalum/aluminum alloys, nickel/chrome alloys (e.g., nichrome), iron/chromium/aluminum alloys (e.g., FeCrAl), copper/nickel alloys, molybdenum alloys, graphite, steel, stainless steel, zinc, alloys including at least nickel, chromium, and iron; molybdenum, molybdenum disilicide ($MoSi_2$), silicon carbide, barium titanate, and lead titanate composites.

Generation of Inertial Bubbles and Acoustic Pressure Waves (FIGS. 7-12)

The catheter systems including superheating systems described herein can heat a balloon fluid within the balloon rapidly enough to achieve spontaneous vaporization of the balloon fluid and generate inertial bubbles and acoustic pressure waves. Exemplary inertial bubbles are depicted by inertial bubbles 126 in FIGS. 1 and 6. Without wishing to be bound by any particular theory, it is believed that the inertial bubbles are generated by superheating a fluid to the point of a spontaneous vaporization of a volume of the fluid. It is believed that superheating a fluid, such as the balloon fluids disclosed herein, can occur when optical or thermal energy is efficiently absorbed by the fluid to result in superheating of the fluid to temperatures greater than two times, three times, or more, than the boiling temperature of the fluid. The superheating of the fluid to such temperatures results in approaching the spinodal limit of the fluid. The superheated fluid becomes unstable to random density fluctuations and an explosive phase transition from a fluid to a vapor takes place to produce a fast-expanding vapor bubble, such as the inertial bubbles described herein.

In the embodiments herein, it is believed that an inertial bubble can form as a result of superheating a volume of the balloon fluid at or near the light windows or resistive heating elements described. The volume of balloon fluid to be superheated at or near the light windows or resistive heating elements has an initial volume prior to being heated. As the volume of balloon fluid at or near the light windows or resistive heating elements is superheated from the light exiting a light window or from the heat generated at a resistive heating element, that volume of the balloon fluid begins to increase temperature and the balloon fluid begins to vaporize and form an inertial bubble during the phase transition from a fluid to a vapor. The inertial bubble continues to form during the superheating process until it has a diameter that is about two times to about ten times the diameter of the initial volume of the balloon fluid prior to heating. In some embodiments, the inertial bubble has a diameter that is greater than ten times the diameter of the initial volume of the balloon fluid prior to heating. It is believed that one or more high-energy inertial acoustic pressure wave fronts will form within a balloon fluid as an inertial bubble expands to its maximum size and then undergoes a cavitation event.

The acoustic pressure waves are generated having pressures in the range of 2 megapascals (MPa) to 25 MPa, as will be discussed in more detail below. The final inertial bubble diameters suitable for use herein can include those from 1 mm to about 25 mm. In some embodiments, the final inertial bubble diameter can be greater than or equal to 0.5 mm 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm, or can be an amount falling within a range between any of the foregoing.

Figure 7:
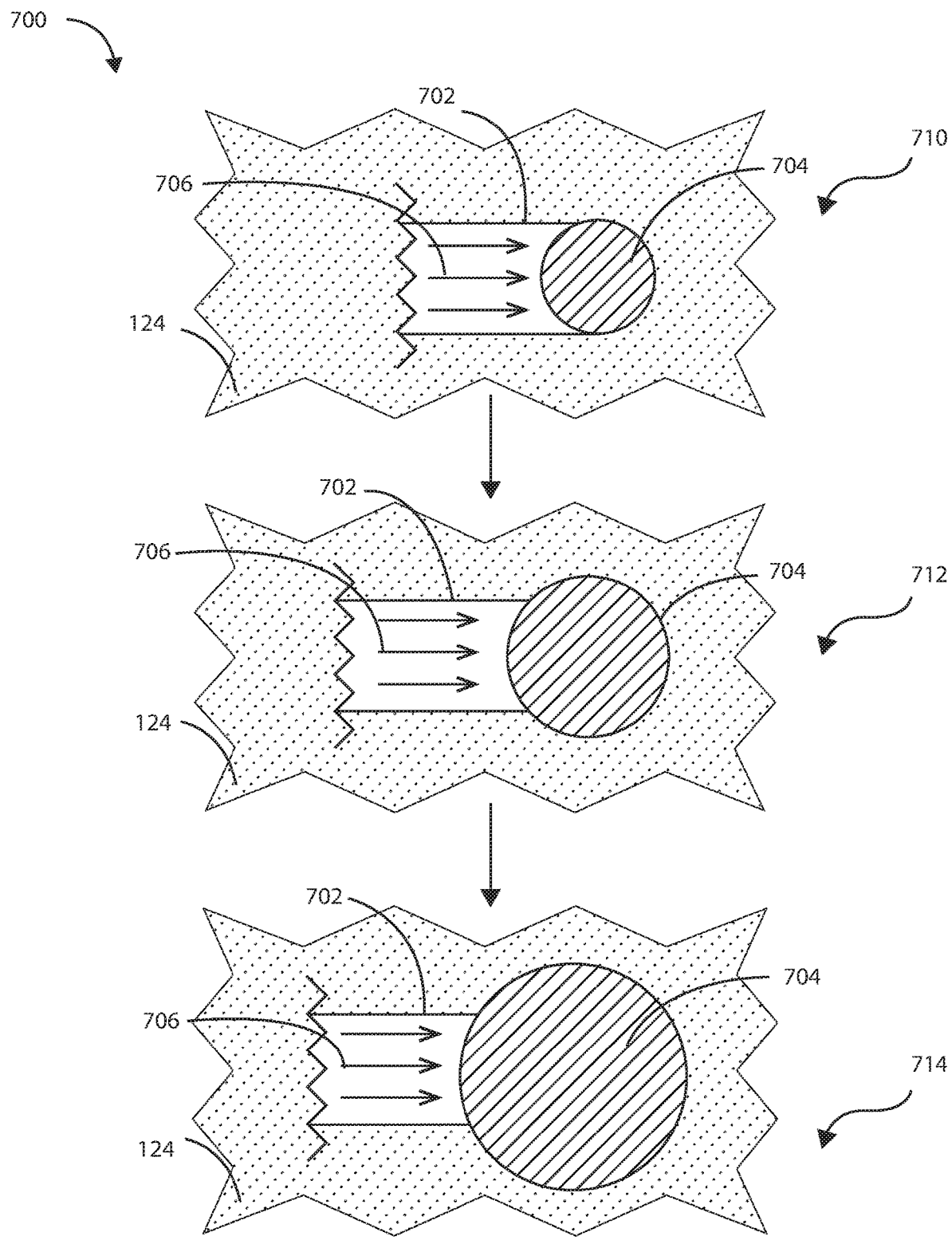
FIG. 7 is a schematic flow diagram of generating an inertial bubble as generated by a catheter in accordance with various embodiments herein.

Referring now to FIG. 7, a schematic flow diagram of a spontaneous vaporization process 700 of a balloon fluid and generation of an inertial bubble is shown in accordance with various embodiments herein. The process of superheating begins at 710 where light or thermal energy 706 is supplied to an initial volume of the balloon fluid 124 at or near the light windows or resistive heating elements the light disposed along the light guide or electrical lead 702. The volume of balloon fluid at or near the light windows or resistive heating elements is superheated rapidly enough to lead to the spontaneous vaporization of that initial volume of balloon fluid to generate an inertial bubble 704. The inertial bubble will have an initial diameter at the instant the spontaneous vaporization of that initial volume of balloon fluid occurs. At 712 the inertial bubble 704 continues to expand and the diameter of the inertial bubble 704 continues to expand. At 714 the expansion of the inertial bubble 704 reaches a maximum and begins to collapse, resulting in a cavitation event. The entire spontaneous vaporization process 700 results in the generation of one or more acoustic pressure waves. The spontaneous vaporization process 700 can occur within zero to five seconds. In some embodiments, the spontaneous vaporization process can occur during a time from greater than or equal to 1 nanosecond (ns), 10 ns, 100 ns, 1 microsecond (µs), 10 µs, 100 µs, 200 µs, 300 µs, 400 µs, 500 µs, 600 µs, 700 µs, 800 µs, 900 µs, 1 millisecond (ms), 10 ms, 20 ms, 30 ms, 40 ms, 50 ms, 60 ms, 70 ms, 80 ms, 90 ms, or 100 ms, 250 ms, 500 ms, 1 second (sec), 2 sec, 3 sec, 4 sec, 5 sec, 6 sec, 7 sec, 8 sec, 9 sec, or 10 sec, or can be an amount falling within a range between any of the foregoing.

The acoustic pressure waves generated by the catheter systems described herein can disrupt a vascular lesion within or adjacent to a vessel of a patient. FIGS. 8-12 show examples of catheters using light energy to disrupt a vascular lesion. Catheters using electrical energy sources could also be constructed similar to FIGS. 8-12 with resistive heating elements located where the light diverting elements and light windows are shown in FIGS. 8-12.

Figure 8:
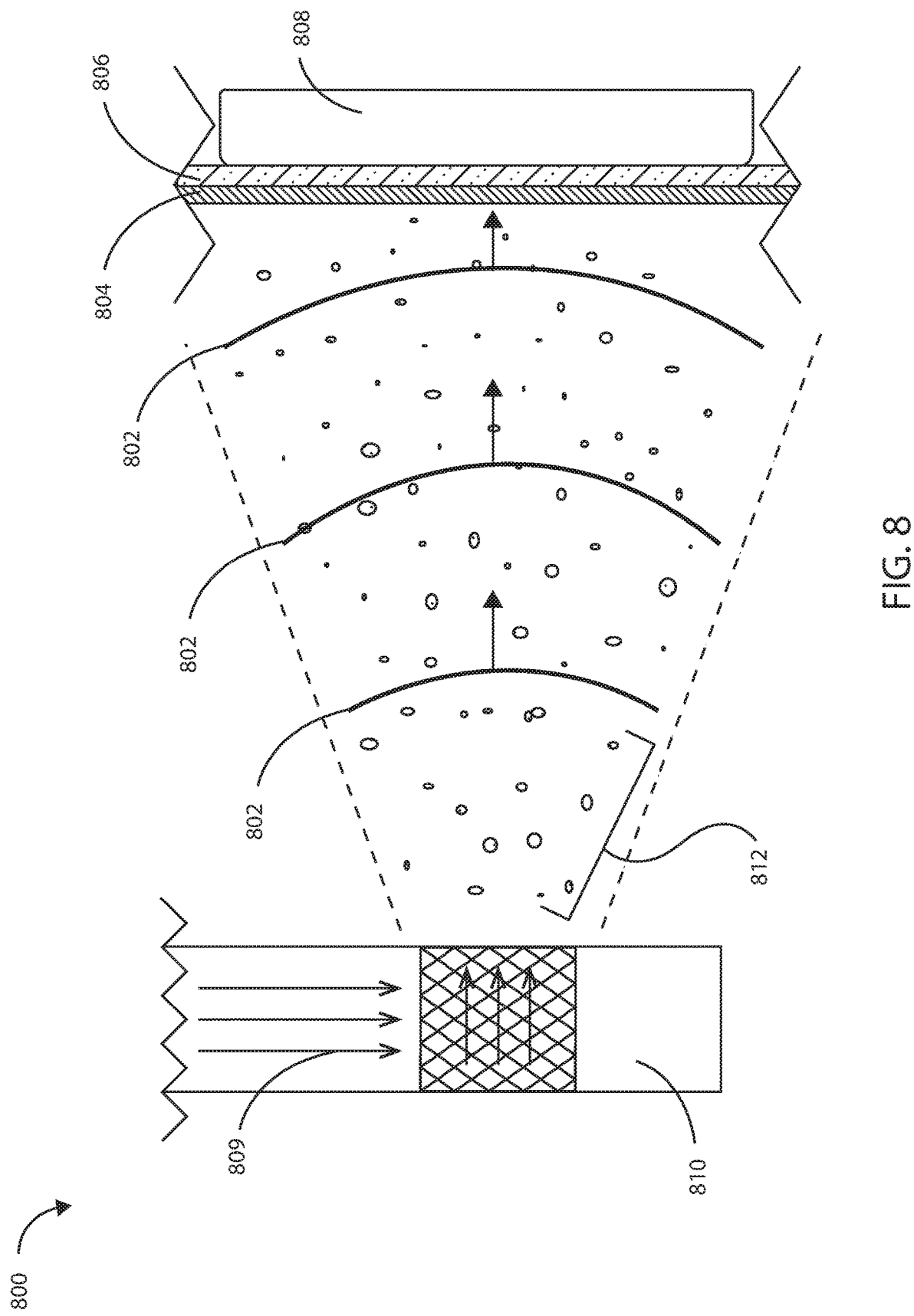
FIG. 8 is a schematic view of an acoustic pressure wave and inertial impulse generated by a catheter in accordance with various embodiments herein.
Figure 9:
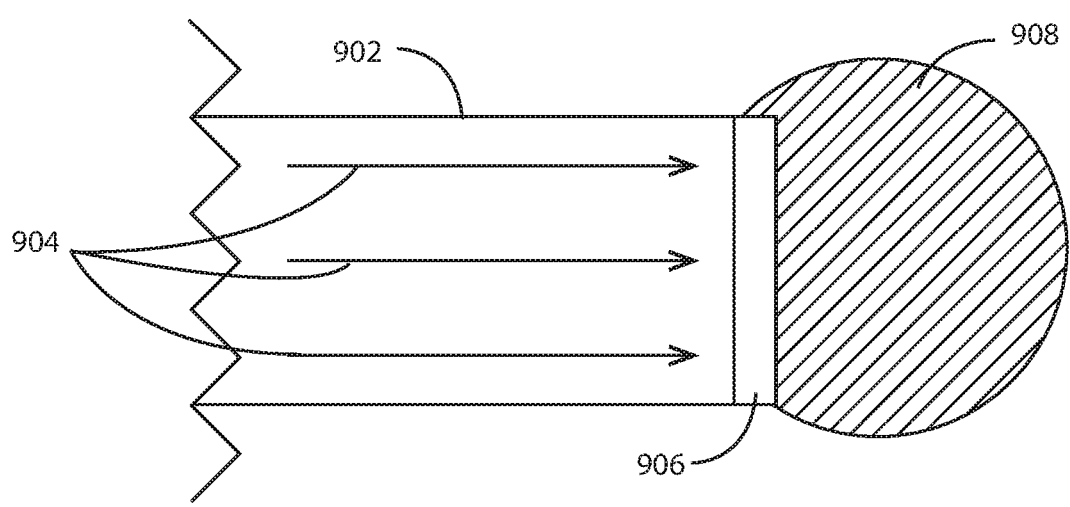
FIG. 9 is a schematic cross-sectional view of a distal portion of a light guide in accordance with various embodiments herein.

Referring now to FIG. 8, a schematic depiction 800 of the collapse of an inertial bubble and the subsequent generation of acoustic pressure waves is shown in accordance with various embodiments herein. Light 809 can be directed from light guide 810 by a diverting element (discussed below), to initiate a superheating of the balloon fluid within a balloon to rapidly achieve spontaneous vaporization of the balloon fluid and to generate an inertial bubble, such as inertial bubble 704 in FIG. 7. The rapid spontaneous vaporization and expansion of the inertial bubble and the subsequent inertial bubble collapse 812 (depicted as small bubbles) can result in formation of one or more acoustic pressure waves 802. Acoustic pressure wave 802 can be directed toward the balloon wall 804 to create an inertial impulse in a vessel wall 806 to transfer momentum to the vascular lesion 808 to result in the disruption the vascular lesion 808.

The light guides herein can include various configurations and one or more light windows distributed along the longitudinal axis. The light guides can be in optical communication with a light source at a proximal portion of a catheter system and the light windows at a distal portion of a catheter system and disposed within a balloon. Referring now to FIGS. 9-12, a schematic views of various configurations for the distal tip of a light guide suitable for use in the catheter systems herein are shown in accordance with various embodiments herein. In the configuration shown in FIG. 9, a schematic view of the distal tip of a light guide 902 is shown. Light guide 902 includes a cylindrical end shape. Light guide 902 is configured such that light 904 travels from a light source (not shown) in the direction from the proximal portion 104 of the light guide 902 to a distal portion of the light guide 902, as indicated by the arrows. Light 904 within light guide 902 is directed from the light guide 902 to the distal tip of the light guide 902 where it exits at a first light window 906. Balloon fluid (not shown) at the distal tip of light guide 902 is heated rapidly enough to achieve spontaneous vaporization of the balloon fluid and generate an inertial bubble 908.

Figure 10:
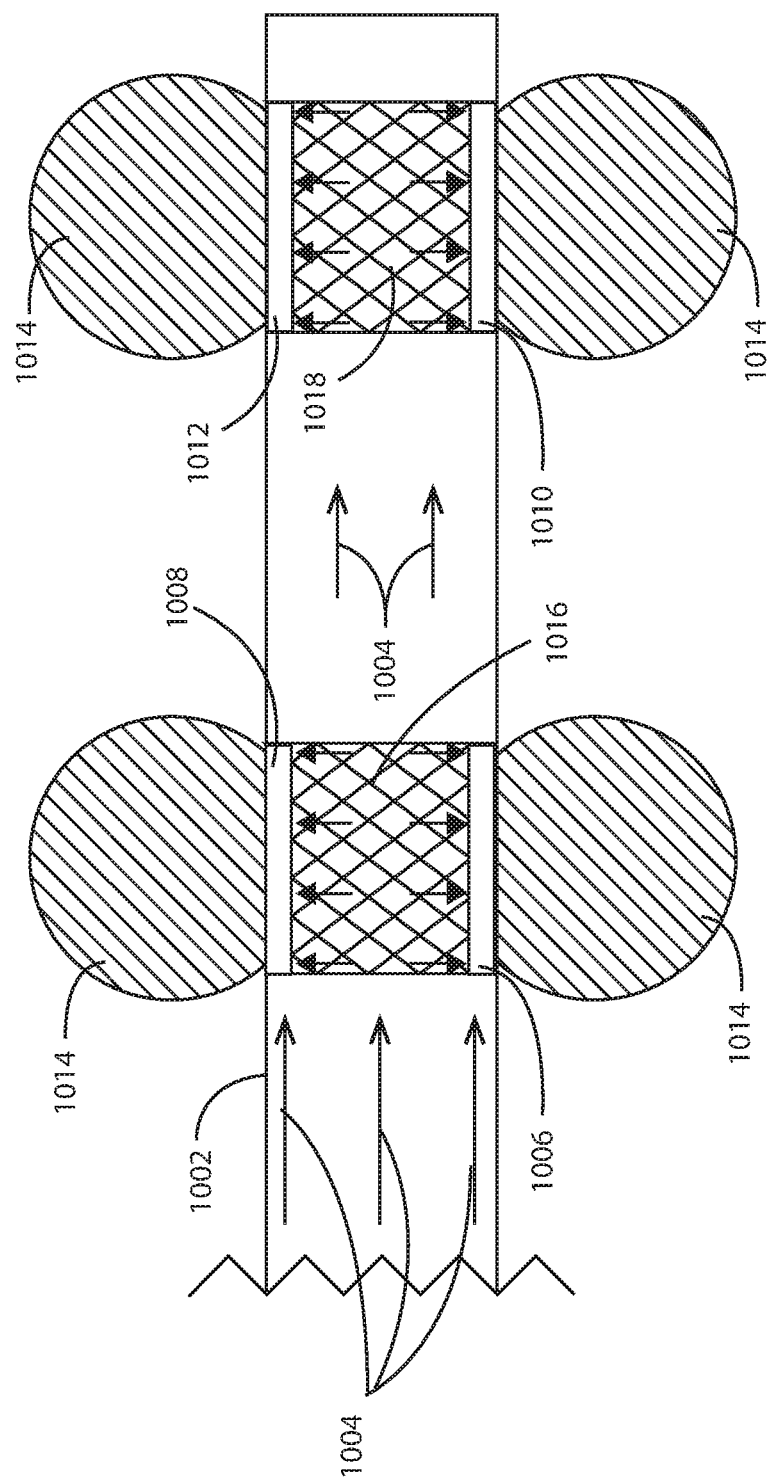
FIG. 10 is a schematic cross-sectional view of an additional embodiment of a distal portion of a light guide in accordance with various embodiments herein.

In the configuration shown in FIG. 10, a schematic view of a distal tip of a light guide 1002 having multiple fiber diffusers disposed therein. Light guide 1002 includes a cylindrical end shape. Light guide 1002 is configured such that light 1004 travels from a light source (not shown) in the direction from the proximal portion of the light guide 1002 to a distal portion of the light guide 1002, as indicated by the arrows. Light 1004 within light guide 1002 is directed within the light guide 1002 to a first fiber diffuser 1016 and a second fiber diffuser 1018 disposed in the distal tip of the light guide 1002. The first fiber diffuser 1016 and the second fiber diffuser 1018 are configured to direct light 1004 from the light guide 1002 to exit the light guide 1002 at a side surface portion of the light guide 1002. In cases where a light guide 1002 includes a first fiber diffuser 1016 to direct light 1004 from the light guide 1002 to exit the light guide 1002 at a side surface portion of the light guide 1002, the side surface portion of the light guide 1002 is in optical communication with at least a first light window 1006 and the light 1004 exits the first light window 1006. In some embodiments, the first fiber diffuser 1016 can also be in optical communication with a second optical window 1008. In some embodiments, an optical window can span the entire circumference of a light guide. In other embodiments, an optical window can span only a portion of the circumference of a light guide.

The second fiber diffuser 1018 is configured to direct light 1004 from the light guide 1002 to exit the light guide 1002 at a side surface portion of the light guide 1002. The second fiber diffuser 1018 can direct light 1004 from the light guide 1002 to exit the light guide 1002 at a side surface portion of the light guide 1002, the side surface portion of the light guide 1002 is in optical communication with at least a third light window 1010 and the light 1004 exits the third light window 1010. In some embodiments, the second fiber diffuser 1018 can also be in optical communication with a fourth optical window 1012. Balloon fluid (not shown) at the distal tip of light guide 1002 is heated rapidly enough to achieve spontaneous vaporization of the balloon fluid and generate one or more inertial bubbles 1014.

Figure 11:
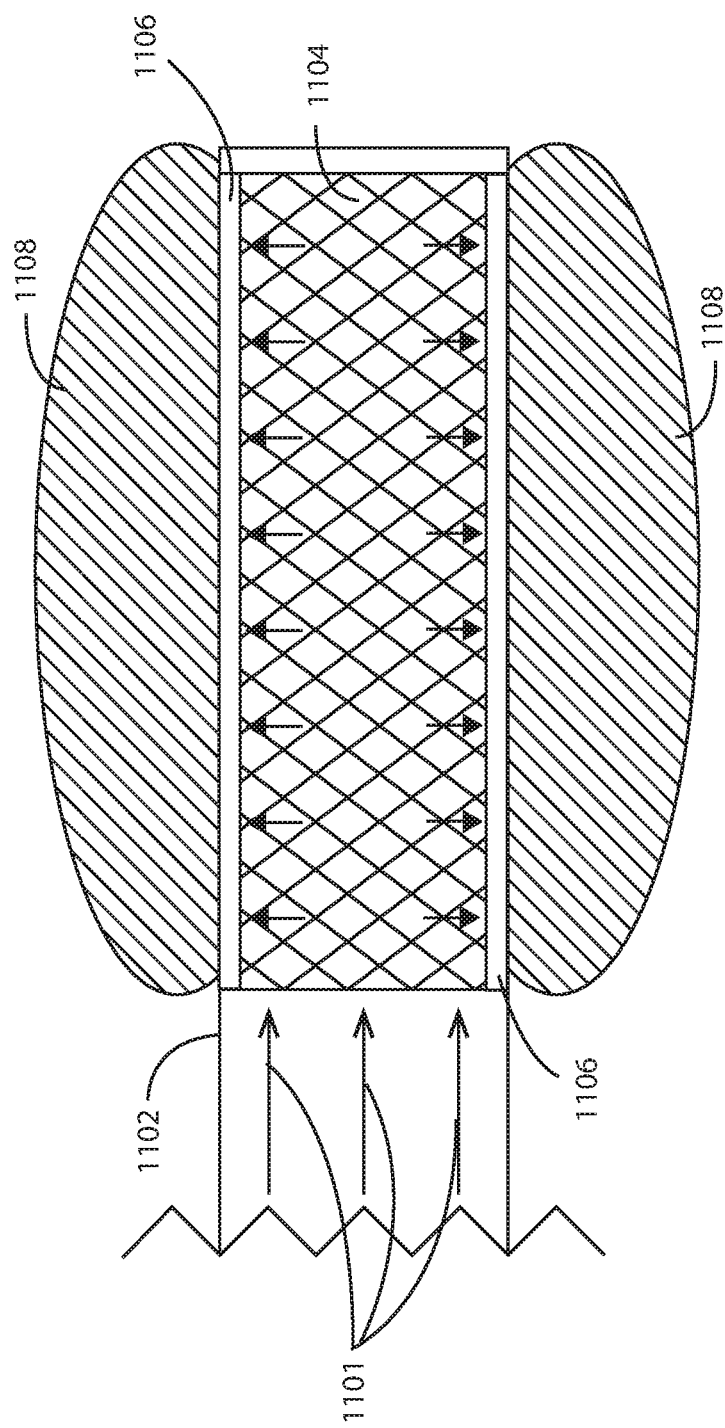
FIG. 11 is a schematic cross-sectional view of a distal portion of a light guide in accordance with various embodiments herein.

In the configuration shown in FIG. 11, a schematic view of a distal tip of a light guide 1102 having a single large fiber diffuser disposed therein. Light guide 1102 includes a single fiber diffuser 1104 positioned along the elongate shaft of the distal region of the light guide 1102. The fiber diffuser 1104 directs light 1101 to exit the light guide 1102 at a side surface portion thereof. The side surface portion of the light guide 1102 is in optical communication with one or more light windows 1106 and fiber diffuser 1104, such that the fiber diffuser 1104 and the one or more light windows 1106 are in optical communication with one another. Balloon fluid (not shown) at the distal tip of light guide 1102 is heated rapidly enough to achieve spontaneous vaporization of the balloon fluid and generate one or more inertial bubbles 1108.

Figure 12:
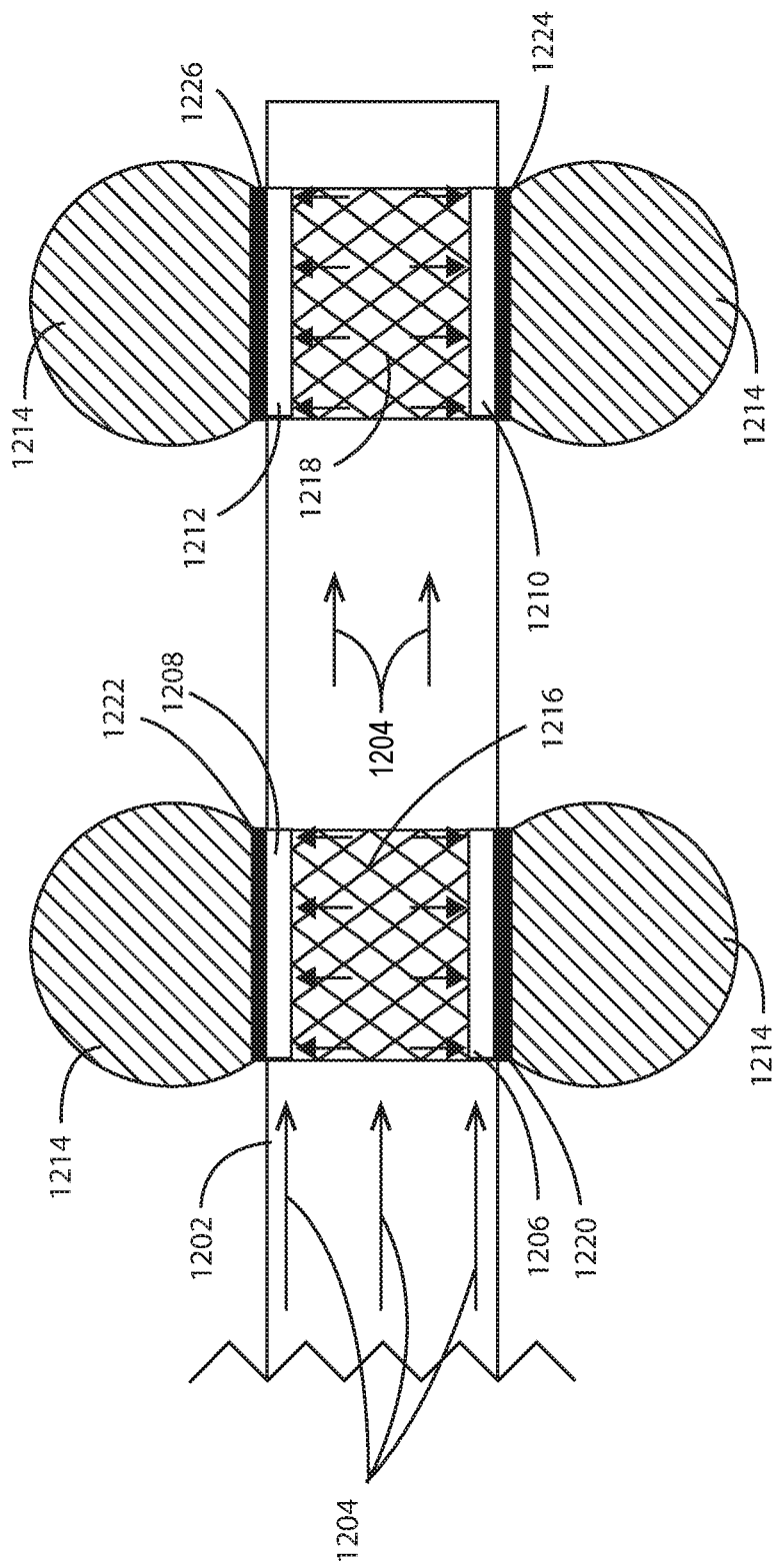
FIG. 12 is a schematic cross-sectional view of a distal portion of a light guide in accordance with various embodiments herein.

In the configuration shown in FIG. 12, a schematic view of a distal tip of a light guide 1202 having multiple fiber diffusers and multiple light windows having a thermally conductive photonic absorption layer disposed thereon. Light guide 1202 includes a cylindrical end shape. Light guide 1202 is configured such that light 1204 travels from a light source (not shown) in the direction from the proximal portion of the light guide 1202 to a distal portion of the light guide 1202, as indicated by the arrows. Light 1204 within light guide 1202 is directed within the light guide 1202 to a first fiber diffuser 1216 and a second fiber diffuser 1218 disposed in the distal tip of the light guide 1202. The first fiber diffuser 1216 and the second fiber diffuser 1218 are configured to direct light 1204 from the light guide 1202 to exit the light guide 1202 at a side surface portion of the light guide 1202. In cases where a light guide 1202 includes a first fiber diffuser 1216 to direct light 1204 from the light guide 1202 to exit the light guide 1202 at a side surface portion of the light guide 1202, the side surface portion of the light guide 1202 is in optical communication with at least a first light window 1206 and light 1204 exits the first light window 1206. In some embodiments, the first fiber diffuser 1216 can also be in optical communication with a second light window 1208. In some embodiments, an optical window can span the entire circumference of a light guide. In other embodiments, an optical window can span only a portion of the circumference of a light guide.

The second fiber diffuser 1218 is configured to direct light 1204 from the light guide 1202 to exit the light guide 1202 at a side surface portion of the light guide 1202. The second fiber diffuser 1218 can direct light 1204 from the light guide 1202 to exit the light guide 1202 at a side surface portion of the light guide 1202, the side surface portion of the light guide 1202 is in optical communication with at least a third light window 1210 and light 1204 exits the third light window 1210. In some embodiments, the second fiber diffuser 1218 can also be in optical communication with a fourth light window 1212. Balloon fluid (not shown) at the distal tip of light guide 1202 is heated rapidly enough to achieve spontaneous vaporization of the balloon fluid and generate one or more inertial bubbles 1214.

The light guide 1202 further includes a first thermally conductive photonic absorption layer 1220 disposed on the first light window 1206, where the first thermally conductive photonic absorption layer 1220 is configured to absorb photonic energy from the light guide 1202 and convert the photonic energy into thermal energy to achieve spontaneous vaporization of a balloon fluid within the balloon and to generate inertial bubbles and acoustic pressure waves. The light guide can further include a second thermally conductive photonic absorption layer 1222 disposed on second light window 1208; a third thermally conductive photonic absorption layer 1224 disposed on third light window 1210; and a fourth thermally conductive photonic absorption layer 1226 disposed on fourth light window 1212. It will be appreciated that more than four thermally conductive photonic absorption layers can be used when more than four light windows are used.

In some embodiments, the light guides can include a thermally conductive photonic absorption layer disposed on any of the light windows. In some embodiments, the light guides can include a thermally conductive photonic absorption layer disposed on all of the light windows. In some embodiments, the light guides can include a thermally conductive photonic absorption layer disposed on a portion of the light windows. The thermally conductive photonic absorption layer can be completely disposed about the light guide or partially disposed about the light guide. The thermally conductive photonic absorption layer can be disposed on a first light window. The thermally conductive photonic absorption layer can be configured to absorb photonic energy from the light guide and convert the photonic energy into thermal energy, heating the thermally conductive photonic absorption layer, which in turn heats the balloon fluid to achieve spontaneous vaporization of the balloon fluid and to generate inertial bubbles and acoustic pressure waves. The thermally conductive photonic absorption layer can include, but is not to be limited to nanoparticles, carbon nanotubes, carbon black, candle soot, candle soot nanoparticles, a nanotube array, multiwall carbon nanotubes, light absorbing dyes, gold nanoparticles, and the like.

Figure 13:
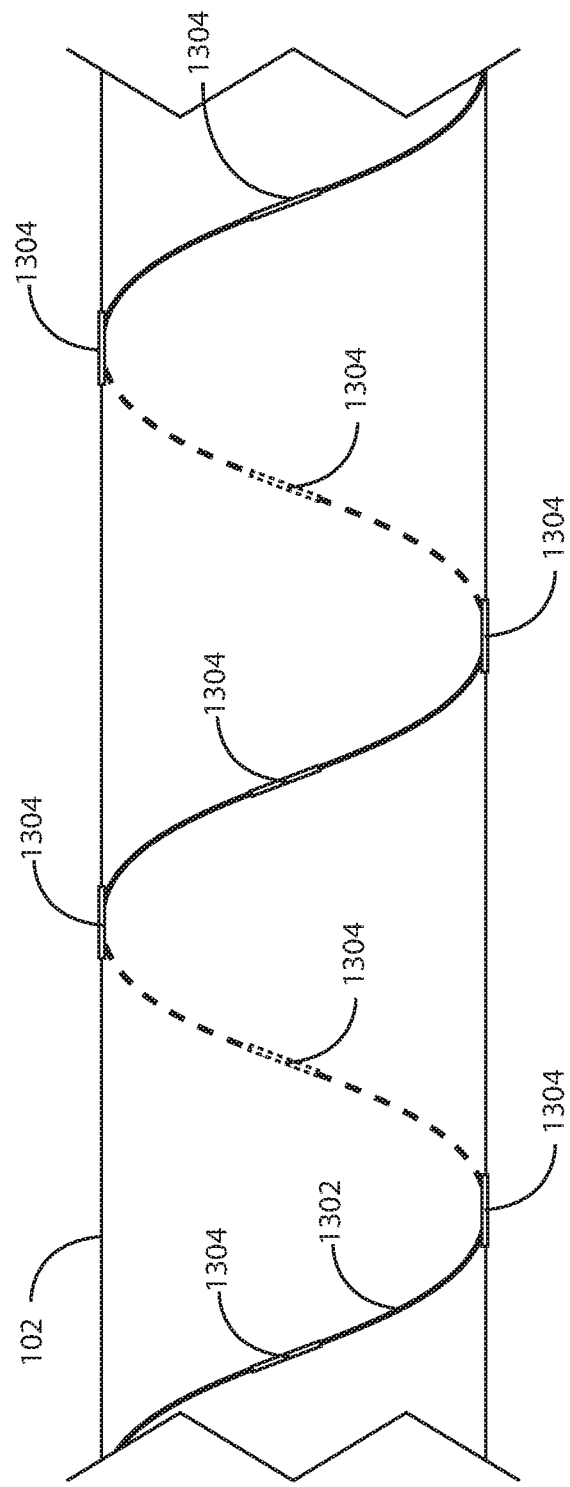
FIG. 13 is a schematic side view of a light guide disposed about an elongate shaft in accordance with various embodiments herein.

Spiral Path for Energy Source (FIG. 13)

In various embodiments herein, the light guides or the electrical leads can be disposed in a spiral configuration about an elongate shaft of the catheter systems herein. Referring now to FIG. 13, a schematic view of a light guide 1302 disposed in a spiral configuration about an elongate shaft 102 is shown in accordance with various embodiments herein. Light guide 1302 includes a plurality of light windows 1304 disposed about the length of the light guide 1302 and disposed axially about the elongate shaft 102. It will be appreciated that the configuration of light windows in light guide 1302 can allow for the generation of inertial bubbles and acoustic pressure waves that can simultaneously be directed toward a balloon wall adjacent to a vascular lesion, and thereby imparting pressure upon the vascular lesion to induce fractures in a treatment site. It will be appreciated that an electrical lead can be disposed in a spiral configuration about an elongate shaft, where resistive heating elements can be included in the place of the light windows as shown in FIG. 13.

Figure 14:
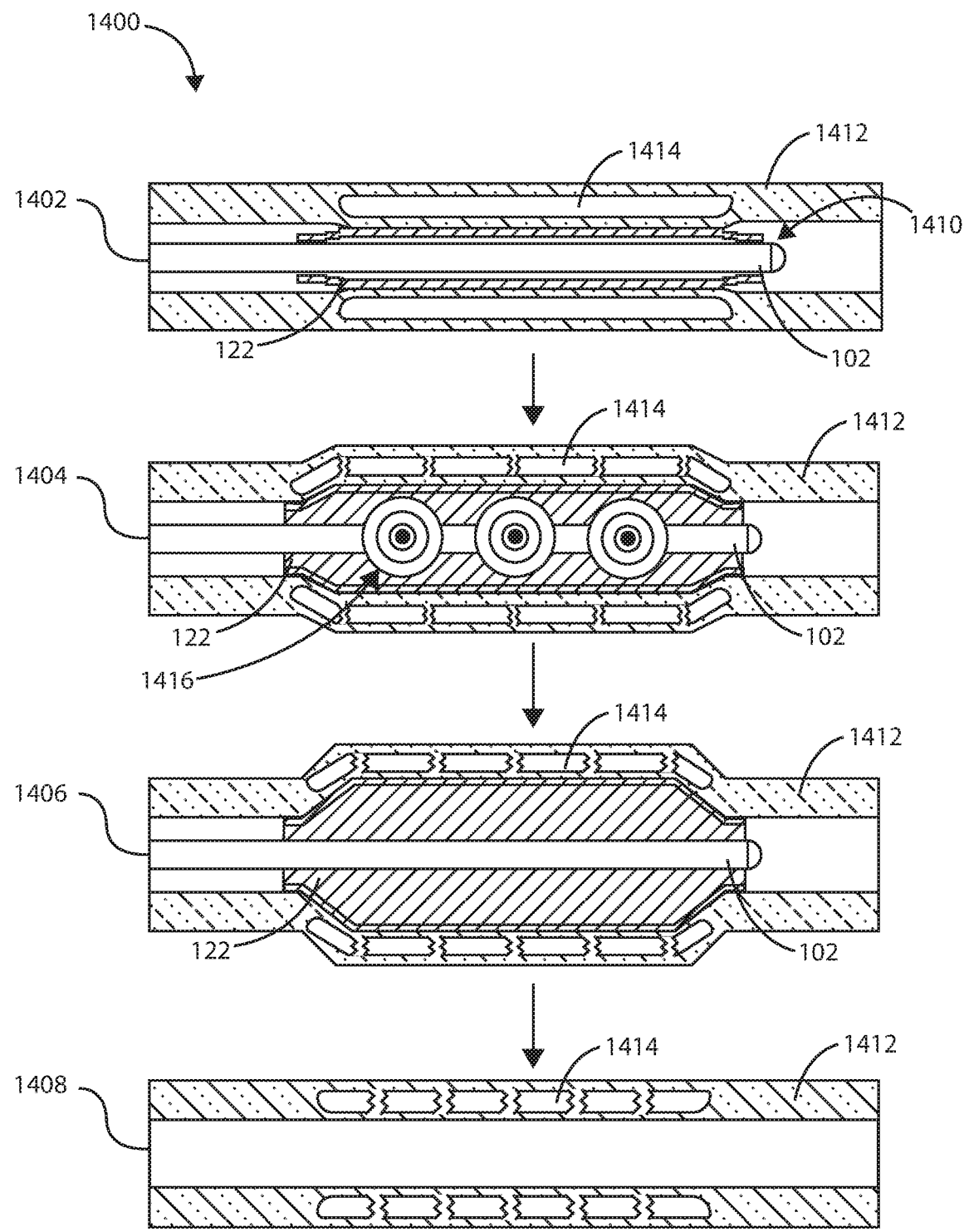
FIG. 14 is a schematic flow diagram for a method in accordance with the various embodiments herein.

Methods (FIG. 14)

The catheters described herein can be used in one or more methods for inducing fractures in a vascular lesion within or adjacent a vessel wall of a blood vessel. Referring now to FIG. 14, a schematic flow diagram for a method 1400 is shown in accordance with the various embodiments herein. Method 1400 includes advancing a catheter 1410 to a treatment site 1414 within the blood vessel 1412, the catheter 1410 including an elongate shaft 102, and a balloon 122 coupled to the elongate shaft 102 at 1402. In some embodiments, the treatment site 1414 can include a vascular lesion location within a patient's vasculature. In some embodiments, the vascular lesion can include a calcified lesion. The method 1400 includes expanding the balloon 122 from a collapsed configuration suitable for advancing the catheter 1410 through a patient's vasculature to a first expanded configuration suitable for anchoring the catheter in position relative to the treatment site 1414 at 1404. The method 1400 includes, after expanding the balloon 122, heating a balloon fluid 124 (illustrated in FIG. 1) in contact with a superheating system to achieve spontaneous vaporization of the balloon fluid 124 and the generation of inertial bubbles 1416 and acoustic pressure waves directed toward a balloon wall, thereby imparting pressure upon the vascular lesion to induce fractures in the treatment site 1414 at 1404.

In some embodiments, the method 1400 includes a first light guide and a first light window in optical communication with a distal portion of the first light guide and disposed within the balloon. In some embodiments, the method 1400 includes a first electrical lead and a first resistive heating element in electrical communication with a distal portion of the first electrical lead and disposed within balloon 122. The method 1400 can also include, after heating the balloon fluid, further expanding the balloon 122 from the first expanded configuration to a second further expanded configuration at 1406. The method can include completely removing the catheter 1410 from the patient's vasculature at 1408.

Heating the balloon fluid, such as in method 1400, can include superheating the balloon fluid to above its boiling point, in less than 10 milliseconds. In some embodiments, heating the balloon fluid, can include superheating the balloon fluid to above its boiling point in more than 1 milliseconds and less than 10 seconds. In some embodiments, heating the balloon fluid, can include superheating the balloon fluid to above its boiling point in more than 1 nanosecond and less than 20 seconds. In some embodiments, heating the balloon fluid can occur during a time from greater than or equal to 1 nanosecond (ns), 10 ns, 100 ns, 1 microsecond (μs), 10 μs, 100 microseconds (μs), 200 μs, 300 μs, 400 μs, 500 μs, 600 μs, 700 μs, 800 μs, 900 μs, 1 millisecond (ms), 10 ms, 20 ms, 30 ms, 40 ms, 50 ms, 60 ms, 70 ms, 80 ms, 90 ms, or 100 ms, 250 ms, 500 ms, 1 second (sec), 2 sec, 3 sec, 4 sec, 5 sec, 6 sec, 7 sec, 8 sec, 9 sec, or 10 sec, 11 sec, 12 sec, 13 sec, 14 sec, 15 sec, 16 sec, 17 sec, 18 sec, 19 sec, or 20 sec, or can be an amount falling within a range between any of the foregoing. In some embodiments, heating the balloon fluid can occur during a time from greater than 20 seconds. In some embodiments, heating the balloon fluid can include superheating the balloon fluid in a range of from 100° C. to 700° C. depending on the composition of the balloon fluid to be used.

The duration of the treatments herein can vary according to the specific treatment site and size of a vascular lesion. In some embodiments, the total treatment time can be from one second to thirty seconds. In some embodiments, the total treatment time can be from five seconds to twenty seconds. In other embodiments, the total treatment time can be from five seconds to ten seconds. The frequency of the superheating process for light pulses or for electric current can be run at a from 1 hertz (Hz) to 100 Hz. In some embodiments, the frequency of the superheating process for light pulses or for electric current can be run at a from 100 Hz to 5000 hertz (Hz).

Balloons

The balloons suitable for use in the catheter systems herein include those that can be passed through the vasculature of a patient when in a collapsed configuration. In some embodiments, the balloons herein are made from silicone. In other embodiments, the balloons herein are made from polydimethylsiloxane (PDMS), polyurethane, polymers such as PEBAX™ material available from Arkema, which has a location at King of Prussia, Pa., USA, nylon, and the like. In some embodiments, the balloons can include those having diameters ranging from 1 millimeter (mm) to 25 mm in diameter. In some embodiments, the balloons can include those having diameters ranging from 1.5 mm to 12 mm in diameter. In some embodiments, the balloons can include those having diameters ranging from 1 mm to 5 mm in diameter. In some embodiments, the diameter can be greater than or equal to 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, 10.5 mm, 11.0 mm, 11.5 mm, 12.0 mm, 12.5 mm, 13.0 mm, 13.5 mm, 14.0 mm, 14.5 mm, 15.0 mm, 15.5 mm, 16.0 mm, 16.5 mm, 17.0 mm, 17.5 mm, 18.0 mm, 18.5 mm, 19.0 mm, 19.5 mm, or 20.0 mm, or can be an amount falling within a range between any of the foregoing.

In some embodiments, the balloons herein can include those having a length ranging from 5 mm to 300 mm in length. In some embodiments, the balloons herein can include those having a length ranging from 8 mm to 200 mm in length. In some embodiments, the length of the balloon can be greater than or equal to 5 mm, 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, or 300 mm, or can be an amount falling within a range between any of the foregoing.

The balloons herein can be inflated to inflation pressures from 1 atmosphere (atm) to 70 atm. In some embodiments, the balloons herein can be inflated to inflation pressures of from 6 atm to 20 atm. In some embodiments, the balloons herein can be inflated to inflation pressures of from 20 atm to 70 atm. In some embodiments, the balloons herein can be inflated to inflation pressures that can be greater than or equal to 1 atm, 10 atm, 20 atm, 30 atm, 40 atm, 50 atm, 60 atm, or 70 atm, or can be an amount falling within a range between any of the foregoing.

The balloons herein can include those having various shapes, including, but not to be limited to, a conical shape, a square shape, a rectangular shape, a spherical shape, a conical/square shape, a conical/spherical shape, an extended spherical shape, an oval shape, a tapered, shape, a bone shape, a stepped diameter shape, an offset shape, or a conical offset shape.

In some embodiments, the balloons herein can provide a therapeutic agent to a treatment site. In some embodiments, the therapeutic agent can be delivered via a drug eluting coating, a drug eluting stent structure, or by the delivery of a drug composition through one or more lumens of the catheters described herein. The drug elution coating or drug eluting stent structure can include one or more therapeutic agents including anti-inflammatory agents, anti-neoplastic agents, anti-angiogenic agents, and the like. Exemplary agents can include, but is not to be limited to paclitaxel, docetaxel, everolimus, and sirolimus, and analogs thereof.

Balloon Fluids

Exemplary balloon fluids suitable for use herein can include, but are not to be limited to one or more of water, saline, contrast agent, fluorocarbons, perfluorocarbons, gases, such as carbon dioxide, and the like. In some embodiments, the balloon inflation fluids include a mixture of saline to contrast agent in a volume ratio of 50:50. In some embodiments, the balloon fluids include a mixture of saline to contrast agent in a volume ratio of 25:75. In some embodiments, the balloon fluids include a mixture of saline to contrast agent in a volume ratio of 75:25. The balloon fluids suitable for use herein can be tailored on the basis of composition, viscosity, and the like in order to manipulate the rate of travel of the acoustic pressure waves therein. The balloon fluids suitable for use herein are biocompatible. A maximum volume of balloon fluid to be subjected to super-heating can be tailored by the chosen light source and the type of balloon fluid used.

In some embodiments, the contrast agents used herein can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12), perfluoro-octane (PFO), perfluoroperhydrophenanthrene, perfluorodecalin (PFD), perfluorotributylamide (PFTB) and perfluorooctylbromide (PFOB), and the like.

The balloon fluids herein can include those that include absorptive agents that can selectively absorb light in the ultraviolet region (e.g., 10 nanometers (nm) to about 400 nm), visible region (e.g., about 400 nm to about 780 nm), and near-infrared region of the electromagnetic spectrum (e.g., about 780 nm to 2.5 µm). Suitable absorptive agents can include those with absorption maxima along the spectrum from 10 nm to 2.5 µm. In some embodiments, the balloon fluids herein can include those that include absorptive agents that have a peak absorption at or near 1.91 µm. In some embodiments, the absorptive agents used herein can be water soluble. In other embodiments, the absorptive agents used herein are not water soluble. In some embodiments, the absorptive agents used in the balloon fluids herein can be tailored to match the peak emission of the light source. Various light sources having emission wavelengths of about 10 nanometers to 10 millimeters are discussed elsewhere herein.

Figure 15:
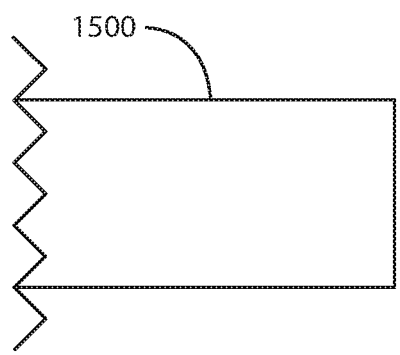
FIGS. 15-17 are schematic axial cross-sectional views of various embodiments of a distal portion of a light guide.
Figure 16:
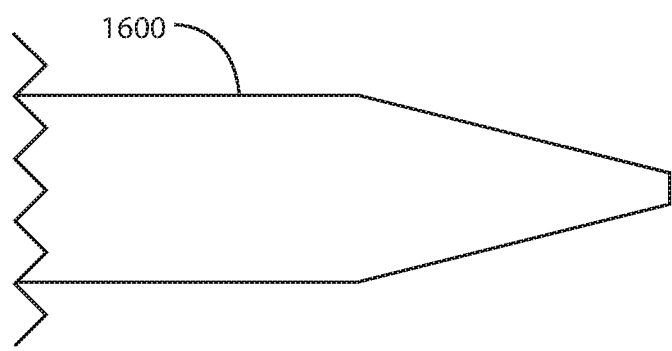
Figure 17:
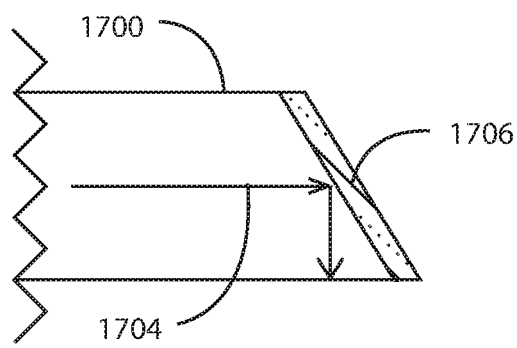
Figure 20:
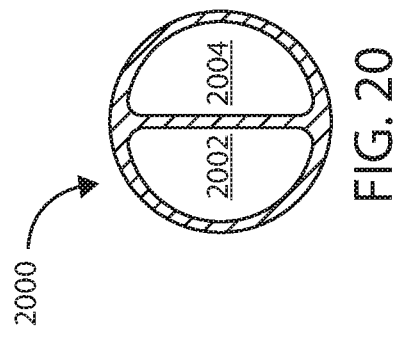
FIGS. 18-29 are schematic axial cross-sectional views of additional embodiments of an elongate shaft of a catheter in accordance with various embodiments herein.
Figure 19:
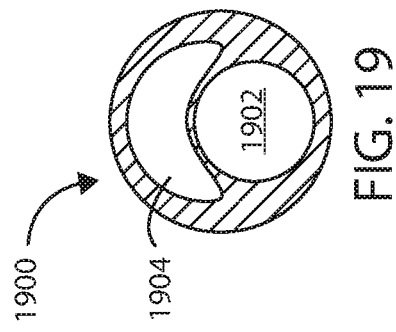

Light Guides (FIGS. 15-17)

The light guides herein can include an optical fiber or flexible light pipe. The light guides herein can be thin and flexible and can allow light signals to be sent with very little loss of strength. The light guides herein can include a core surrounded by a cladding about its circumference. In some embodiments, the core can be a cylindrical core or a partially cylindrical core. The core and cladding of the light guides can be formed from one or more materials, including but not limited to one or more types of glass, silica, or one or more polymers. The light guides may also include a protective coating, such as a polymer. It will be appreciated that the index of refraction of the core will be greater than the index of refraction of the cladding.

Each light guide can guide light along its length to a distal portion having at least one optical window. The light guides can create a light path as portion of an optical network including a light source. The light path within the optical network allows light to travel from one part of the network to another without being modified. Both the optical fiber or the flexible light pipe can provide a light path within the optical networks herein.

The light guides herein can assume many configurations about the elongate shaft of the catheters described herein. In some embodiments, the light guides can run parallel to the longitudinal axis of the elongate shaft of the catheter. In some embodiments, the light guides can be disposed spirally or helically about the longitudinal axis of the elongate shaft of the catheter. In some embodiments, the light guides can be physically coupled to the elongate shaft. In other embodiments, the light guides can be disposed along the length of the outer diameter of the elongate shaft. In yet other embodiments the light guides herein can be disposed within one or more light guide lumens within the elongate shaft. Various configurations for the elongate shafts and light guide lumens will be discussed below.

The light guides herein can include one or more diverting features configured to direct light within the light guide toward a side surface portion of the distal portion of the light guide. The diverting feature can include a reflecting element, a refracting element, a fiber diffuser, or any combination thereof, and a first light window positioned on the side surface portion. When light guides include a diverting feature configured to direct light within the light guide toward a side surface portion of the distal portion of the light guide, the light guides can also include at least a first light window positioned on a side surface portion of the light guide. In some embodiments the light windows span the entire circumference of the light guides, while in other embodiments the light windows only span a portion of the circumference of the light guides. Other properties of the light guides, including size, spacing, and distribution are described elsewhere herein.

In various embodiments, the light guides herein include one or more fiber diffusers. In some embodiments, a light guide can include a first fiber diffuser in a distal portion of the light guide, where the first fiber diffuser directs light from the light guide to exit the light guide at a side surface portion of the light guide. In cases where a light guide includes a first fiber diffuser to direct light from the light guide to exit the light guide at a side surface portion of the light guide, the side surface portion of the light guide is in optical communication with a first light window. In some embodiments the light windows span the entire circumference of the light guides, while in other embodiments the light windows only span a portion of the circumference of the light guides.

In yet other embodiments, the light guides herein can include a plurality of light windows and a plurality of fiber diffusers in the distal portion of the light guide. The plurality of light windows can include a first light window and the plurality of fiber diffusers can include the first fiber diffuser. Each fiber diffuser can direct light from the light guide to exit the light guide at a side surface portion of the light guide, where each side surface portion is in optical communication with one of the plurality of light windows. The plurality of light windows can be axially spaced apart with at least one intervening non-emitting portion of the light guide disposed between each of the plurality of light windows. The side surface portion can be a cylindrical side surface portion and a first light window can be configured as a cylindrical window.

In some embodiments, the light guides can include a thermally conductive photonic absorption layer disposed on any of the light windows. The thermally conductive photonic absorption layer can be disposed on a first light window. The thermally conductive photonic absorption layer can be configured to absorb photonic energy from the light guide and convert the photonic energy into thermal energy to achieve spontaneous vaporization of a balloon fluid within the balloon and to generate inertial bubbles and acoustic pressure waves.

The light guides herein can include various configurations at a distal portion of the light guide. Referring now to FIGS. 15-17, schematic cross-sectional views of the distal portions of various shaped light guides are shown in accordance with various embodiments herein. In FIG. 15, a schematic cross-sectional view of a light guide 1500 is shown. Light guide 1500 includes a cylindrical end shape. In some embodiments, the end of the light guide can have a tapered shape. By way of example, in FIG. 16 a schematic cross-sectional view of a light guide 1600 having a tapered end shape is shown. In some embodiments, the end of the light guide can have an angled shape. By way of example, in FIG. 17 a schematic cross-sectional view of a light guide 1700 is shown. Light guide 1700 includes an angled end shape. The light guide 1700 also includes a diverting feature 1706 at the distal portion to direct the light 1704 within the light guide toward the side surface portion of the light guide. Light guide 1700 is configured such that light 1704 travels from a light source (not shown) in the direction from the proximal portion 104 of the light guide to the distal portion of the light guide 1700, as indicated by the arrow. Upon contact with the diverting feature 1706, the light 1704 is diverted, or reflected, within the light guide 1700.

In some embodiments, a diverting feature can be included with the light guide to direct light toward a side surface portion of the distal portion of the light guide. A diverting feature can include any feature of the system herein that diverts light from the light guide away from its axial path toward a side surface portion of the light guide. Examples include a reflector, a refracting structure, and a fiber diffuser. Fiber diffusers will be discussed in more detail below.

In other embodiments, the light guides can form a spiral configuration about the longitudinal axis of the elongate shaft of the catheter. In some embodiments, the spiral configuration can run clockwise about the longitudinal axis of the elongate shaft of the catheter, while in other embodiments the spiral configuration can run counter-clockwise about the longitudinal axis of the elongate shaft of the catheter. In some embodiments, the light guides can form a single helix, a double helix, a triple helix, or a quadruple helix about the longitudinal axis of the elongate shaft of the catheter.

The light guides herein can come in various sizes and configurations. The light guides will have a longitudinal axis along the elongate shaft of the light guide and short axis about its circumference. In some embodiments, the light guides can have an outer diameter of about 100 μm, including the cladding and the core. In other embodiments, the light guides can include those that have an outer diameter of from 50 μm to 1000 μm including the cladding and the core. The length of the light guides can include those having a length of from 40 cm to 175 cm. In some embodiments, the length of the light guides can include those having a length of from 50-150 cm. In some embodiments, the length of the light guide can include those having a length of 40 cm, 50 cm, 60 cm, 70 cm, 80 cm, 90 cm, 100 cm, 125 cm, 150 cm, or 175 cm. It will be appreciated that the light guides herein can have a usable length that can fall within a range, wherein any of the forgoing lengths can serve as the lower or upper bound of the range, provided that the lower bound of the range is a value less than the upper bound of the range.

It will be appreciated that one or more light guides herein can be adhered to the outer surface of the elongate shaft of a catheter, to create a catheter. However, in other embodiments, one or more light guides can be disposed within a lumen of a catheter. In addition, the catheter may define a lumen for a guidewire having an inner diameter of about 0.014 inch (0.356 mm). In some embodiments, the catheter can include those having an inner diameter of about 0.018 inch (0.457 mm). In yet other embodiments, the catheter can include those having an inner diameter of about 0.035 inch (0.889 mm). In some embodiments the light guides herein can be integrated with a balloon catheter. In some embodiments the light guides herein can be integrated into a guidewire. In embodiments where the light guide is integrated into a guidewire, the resulting catheter can be used independently or can be used with various other balloon catheters.

Leads

The electrical leads convey energy from a generator outside of a patient's body to one or more resistive heaters inside the catheter inside of a patient's body. The leads are configured to electrically connect the resistive heater of the catheter to an external generator. The leads can be situated in a number of different configurations, based on the particular implementation of the catheter. For example, a coaxial lead can be provided with an inner conductor and an outer conductor. In alternative examples, a wire positioned within a lumen, on an inner surface, or on an outer surface of the elongate shaft can be used as a lead. In alternative examples, a lead can be a conductive trace within a lumen, on an inner surface, or on an outer surface of the elongate shaft. Each resistive heater is provided with at least one lead. A separate lead can be provided for each resistive heater. One example of a conductor that can be used is stainless steel. One other example of a conductor that can be used is copper.

Lumens of the Elongate Shaft (FIGS. 18-29)

The elongate shafts herein can include one or more lumens that span the length of the elongate shaft. Referring now to FIGS. 18-29, schematic cross-sectional views of various embodiments of an elongate shaft having multiple lumens are shown in accordance with various embodiments herein. In some embodiments, the elongate shaft can define a guidewire lumen. In some embodiments, the elongate shaft defines an inflation lumen surrounding the guidewire lumen, where the inflation lumen is in fluid communication with a balloon at a distal portion of the elongate shaft. In other embodiments, the elongate shaft defines an inflation lumen disposed alongside the guidewire lumen, where the inflation lumen is in fluid communication with a balloon at a distal portion of the elongate shaft. The elongate shaft can further define at least one control lumen, at least one light guide lumen, or at least one electrical lead lumen.

Figure 18:
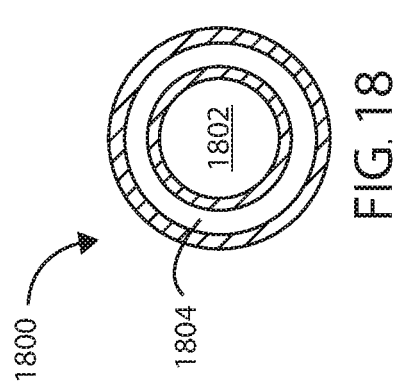
Figure 23:
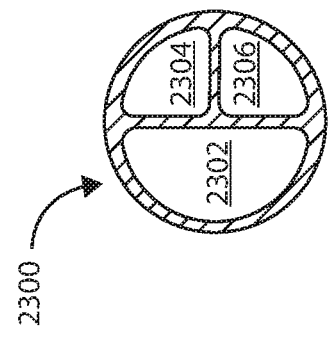
Figure 22:
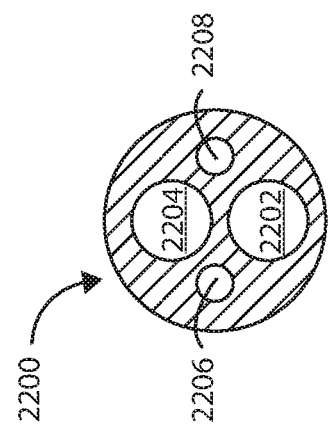
Figure 21:
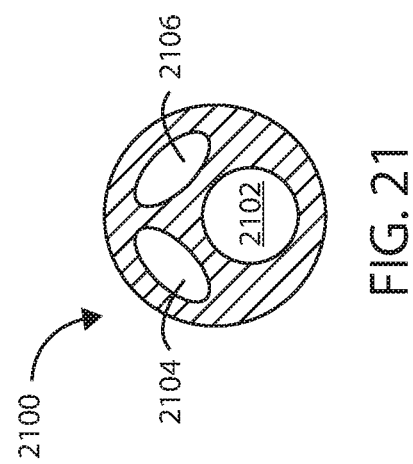
Figure 24:
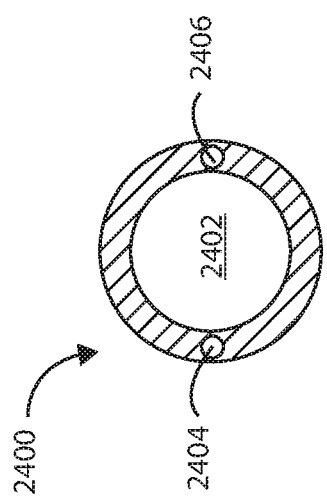
Figure 25:
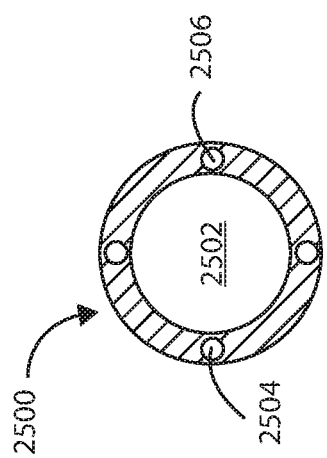
Figure 26:
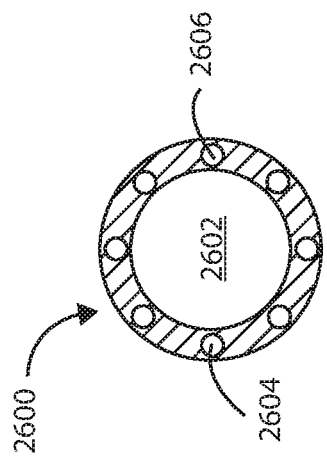
Figure 27:
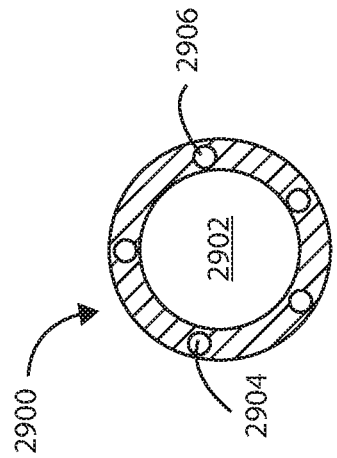
Figure 28:
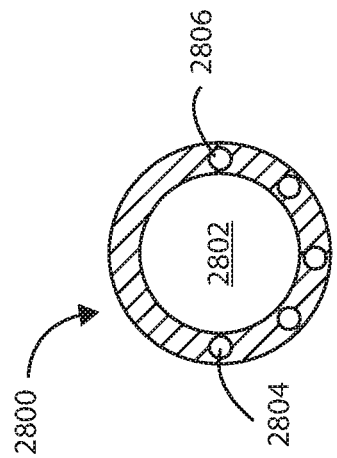
Figure 29:
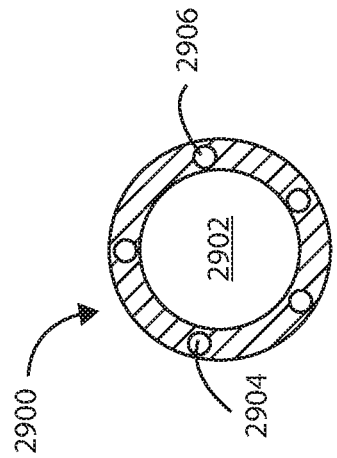

In the configuration in FIG. 18, elongate shaft 1800 includes concentrically disposed guidewire lumen 1802 and an inflation lumen 1804. In the configuration in FIG. 19, elongate shaft 1900 includes guidewire lumen 1902 and an inflation lumen 1904 disposed adjacent to and partially surrounding guidewire lumen 1902. In the configuration in FIG. 20, elongate shaft 2000 includes guidewire lumen 2002 and an inflation lumen 2004 disposed adjacent to guidewire lumen 2002. In the configuration in FIG. 21, elongate shaft 2100 includes guidewire lumen 2102, inflation lumen 2104, and a control lumen 2106. It will be appreciated that the control lumens herein can be used for many purposes, including, but not to be limited to, blood flow, cooling or heating fluid flow, delivery of a diagnostic or therapeutic agent, a light guide lumen, an electrical lead lumen, an inflation lumen, and the like. In the configuration in FIG. 22, elongate shaft 2200 includes guidewire lumen 2202, inflation lumen 2204, and two control lumens 2206 and 2208. In the configuration in FIG. 23, elongate shaft 2300 includes guidewire lumen 2302, inflation lumen 2304, and control lumens 2306.

The light guides or electrical leads can be disposed within one or more energy source lumens disposed within the elongate shafts symmetrically about the circumference. In the configuration in FIG. 24, elongate shaft 2400 includes guidewire lumen 2402, energy source lumen 2404, and control lumen 2406. One or more of lumens 2402, 2404, and 2406 can serve as an inflation lumen. In the configuration in FIG. 25, elongate shaft 2500 includes guidewire lumen 2502, energy source lumen 2504, and control lumen 2506. Elongate shaft 2500 includes two additional lumens that can both be configured as energy source lumens, control lumens, or both an energy source lumen and control lumen. One or more of lumens 2502, 2504, and 2506 can serve as an inflation lumen. In the configuration in FIG. 26, elongate shaft 2600 includes guidewire lumen 2602, energy source lumen 2604, and control lumen 2606. Elongate shaft 2600 includes six additional lumens that can be configured as inflation lumens, energy source lumens, control lumens, or any combination of inflation lumens, energy source lumens, and control lumens.

The light guides or electrical leads can be disposed within one or more energy source lumens disposed within the elongate shafts asymmetrically about the circumference. In the configuration in FIG. 27, elongate shaft 2700 includes guidewire lumen 2702, energy source lumen 2704, and control lumen 2706. Elongate shaft 2700 includes one additional lumen that can be configured as an inflation lumen, an energy source lumen, or a control lumen. In the configuration in FIG. 28, elongate shaft 2800 includes guidewire lumen 2802, energy source lumen 2804, and control lumen 2806. Elongate shaft 2800 includes three additional lumens that can be configured as inflation lumens, energy source lumens, control lumens, or any combination of energy source lumens and control lumens. In the configuration in FIG. 29, elongate shaft 2900 includes guidewire lumen 2902, energy source lumen 2904, and control lumen 2906. Elongate shaft 2900 includes three additional lumens that can be configured as inflation lumens, energy source lumens, control lumens, or any combination of inflation lumens, energy source lumens and control lumens.

It will be appreciated that the lumens described in FIGS. 18-29 can assume many shapes, including, but not to be limited to, circular shape, square shape, crescent shape, triangular shape, and the like. The lumens of the elongate shafts can by symmetrically disturbed in the elongate shaft, asymmetrically distributed, or concentrically distributed. It will be further appreciated that the light guide lumens herein can be coated along the longitudinal length of the elongate shaft with a reflective material capable of propagating light along the elongate shaft from a distal light source to the proximal portion of the catheter, so that the lumen itself can act as a light guide without a separate fiber optic structure.

Figure 30:
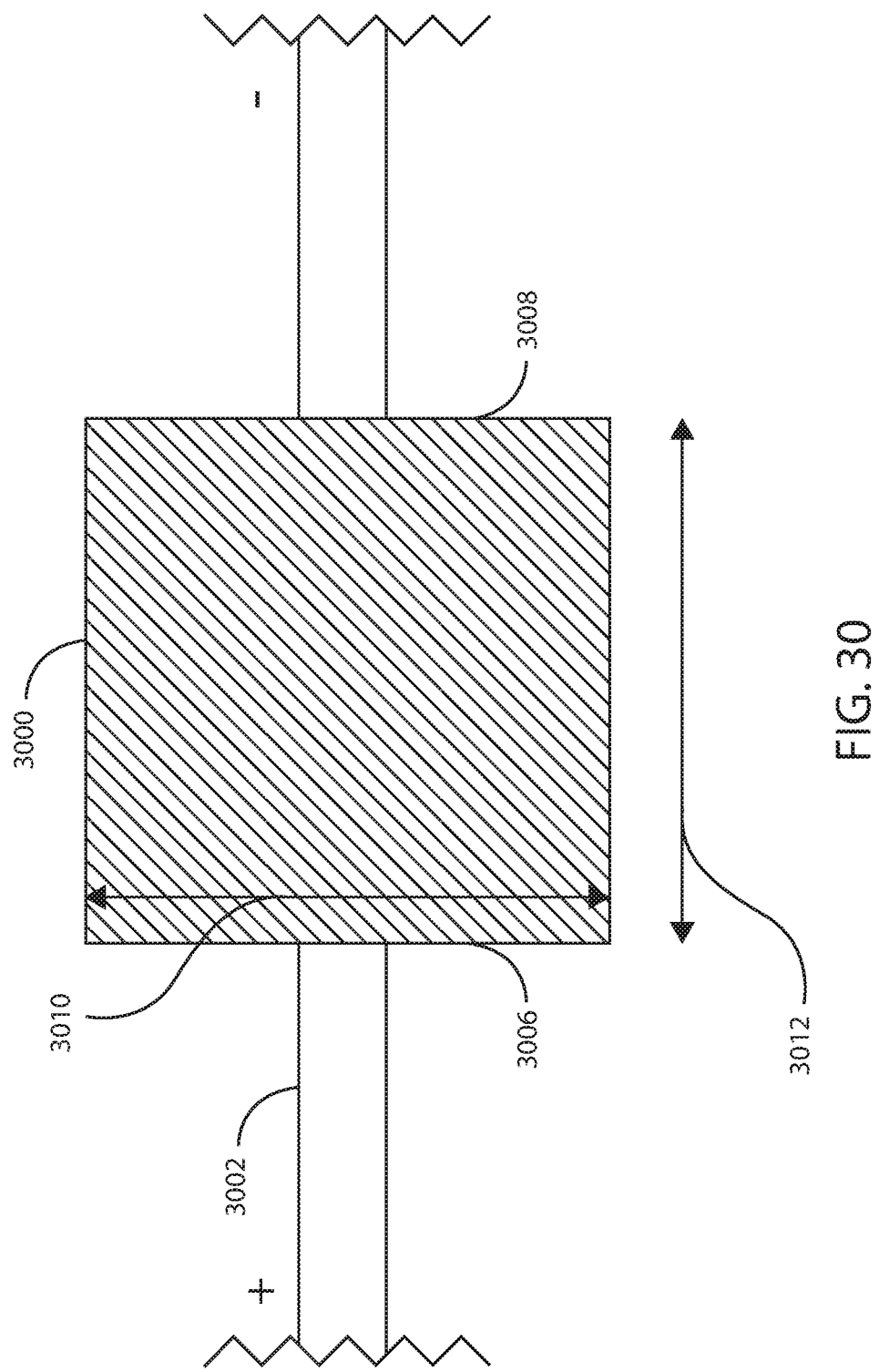
FIG. 30 is a schematic view of a thin-film resistive heater in accordance with the various embodiments herein.
Figure 31:
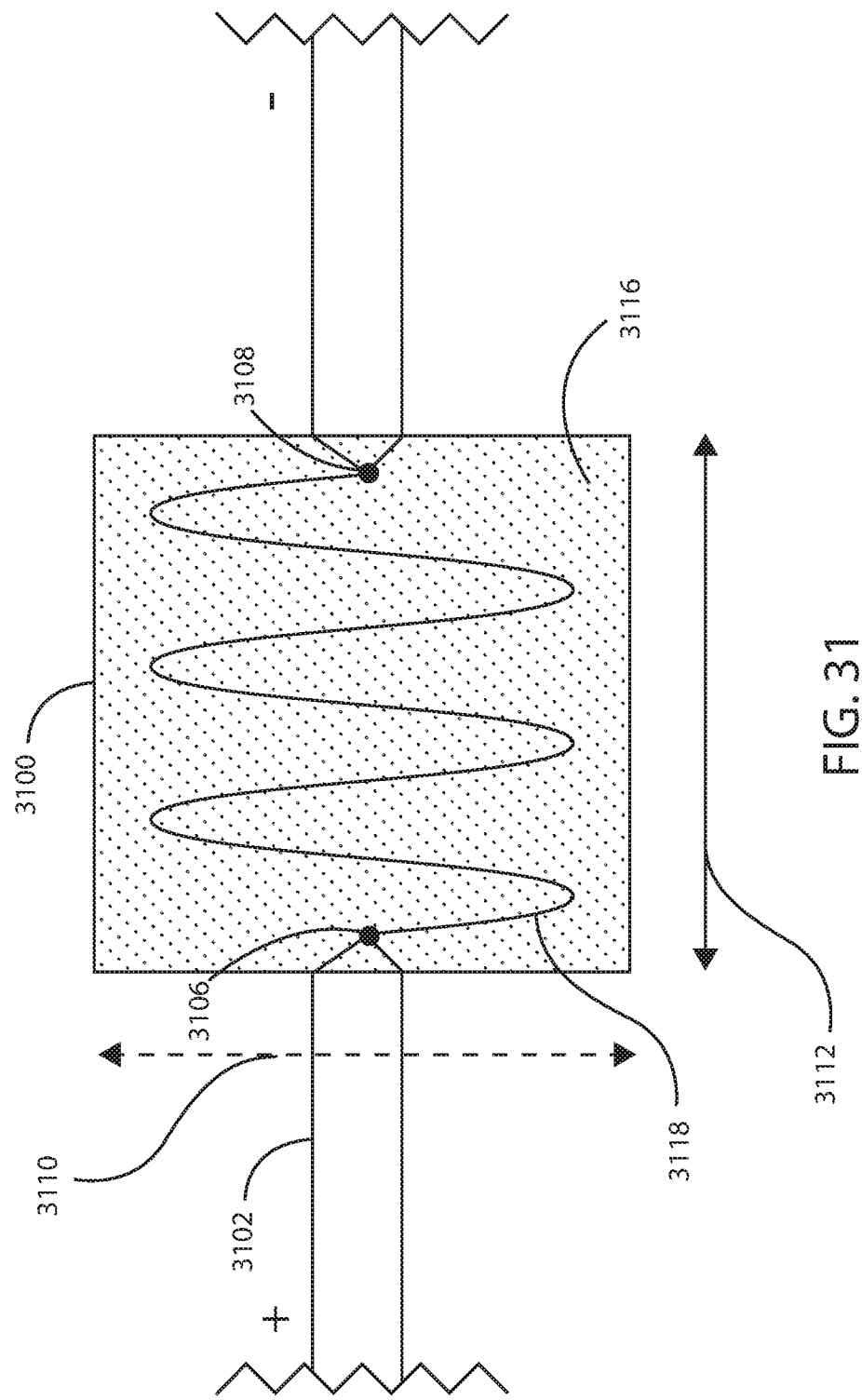
FIG. 31 is a schematic view of a wire heater in accordance with the various embodiments herein.

Resistive Heaters (FIGS. 30 & 31)

Suitable resistive heating elements can include hot filament elements, such as a low voltage electric heater or microheater elements. In some embodiments, the heating element can be a thin microfilm heater. In some embodiments, the heating element can be a wire heater on a substrate. The heating elements described herein can be made from materials that, include, but are not to be limited to those made from tungsten, aluminum, brass, carbon, copper, platinum, tantalum, tantalum/aluminum alloys, nickel/chrome alloys (e.g., nichrome), iron/chromium/aluminum alloys (e.g., FeCrAl), copper/nickel alloys, molybdenum alloys, tungsten alloys, graphite, steel, stainless steel, zinc, alloys including at least nickel, chromium, and iron; molybdenum, molybdenum disilicide ($MoSi_2$), silicon carbide, barium titanate, and lead titanate composites.

To achieve superheating and spontaneous vaporization, the rate of heating the balloon fluid must be sufficiently high, typically on the order of $10^5$ to $10^7$ K/s (kelvins per second). Resistive heating elements with small thermal mass can obtain high heating rates. One exemplary structure for obtaining a high heating rate is thin-film resistive heaters of sub-micron thickness deposited on a substrate with low thermal conductivity. Referring now to FIG. 30 a schematic top-down view of a thin-film resistive heater 3000 is shown in accordance with various embodiments herein. Thin-film resistive heater 3000 can be in electrical communication with lead 3002, where a voltage potential exists across the thin-film resistive heater 3000. In FIG. 30, the positive potential exists at a first side 3006 and the negative potential exists at the second side 3008. It will be appreciated that in some embodiments, the first side 3006 having a negative potential can be on a proximal side of the heater and the second side 3008 having a positive potential can be on a distal side of the heater, or the reverse can be true. The thin-film resistive heaters can assume many shapes, including, but not to be limited to squares, circles, rectangles, parallelograms, triangles, and the like. The dimensions of the thin-film resistive heaters can include a height 3010 and a width 3012. The dimensions of the thin-film resistive heaters can further include a film thickness (not shown in FIG. 30). The width of the thin-film resistive heaters can be from 10 µm to 10 millimeters (mm) and the length of the thin-film resistive heaters can be from 10 µm to 10 mm. The thin-film resistive heaters can have a film thickness of from 1 nanometer (nm) to 100 micrometers (µm).

One example is a thin-film resistive heater structured as those contained within a thermal ink jet printhead sold as HP 51604A Ink Cartridge, commercially-available from Hewlett-Packard, as, Zhao et al., "Pressure and Power Generation during Explosive Vaporization on a Thin-Film Microheater," International Journal of Heat and Mass Transfer 43 (2000) 281-296. Other options for resistive heaters are described in U.S. Pat. Nos. 6,460,966 and 8,369,696 and in U.S. Patent Application 2004/0178879, which are hereby incorporated herein in their entireties.

The resistive heaters herein can also include a hot filament resistive heater. In some embodiments, the hot filament resistive heaters herein can include a wire heater. Referring now to FIG. 31 a schematic top-down view of a wire heater 3100 is shown in accordance with various embodiments herein. The wire heater 3100 can be in electrical communication with lead 3102, where a voltage potential exists across a wire 3118 of the wire heater 3100. In FIG. 31, the positive potential exists at a first end point 3106 of the wire 3118 and the negative potential exists at a second end point 3108 of the wire 3118. It will be appreciated that in some embodiments, the first end point 3106 having a negative potential can be on a proximal side of the heater and the second end point 3108 having a positive potential can be on a distal side of the heater, or the reverse can be true. Alternatively, the first end point 3106 having a negative potential can be on a lateral side of the heater and the second end point 3108 having a positive potential can be on an opposite lateral side of the heater.

The wire 3118 is on a substrate 3116. The substrate 3116 can be made from non-conducting materials such as polymers and ceramics.

The wire heaters can assume many shapes, including, but not to be limited to squares, circles, rectangles, parallelograms, triangles, and the like. In FIG. 31, the wire includes a first end point, and second end point, and a serpentine portion between the first end point and second end point.

The dimensions of the wire heaters can include a height 3110 and a width 3112. The dimensions of the wire heaters can further include a trace, or wire, thickness (not shown in FIG. 31). The width of the substrate of the wire heaters 3100 can be from 10 µm to 10 millimeters (mm) and the length of the substrate of the wire heaters 3100 can be from 10 µm to 10 mm. A thickness of the trace or wire 3118 can be from 1 nanometer (nm) to 100 micrometers (µm).

Fiber Diffusers

A fiber diffuser directs light from within a light guide to exit at a side surface portion of the light guide. The fiber diffusers described herein can be created several ways. In some embodiments, the fiber diffusers can be created by micro-machining the surface of the distal portion of a light guide with a $CO_2$ laser. In some embodiments, a fused silica coating can be applied to the distal portion of the light guide. In other embodiments, the fiber diffuser can be formed from a glass, a polymer, or a metal coating on the distal portion of the light guide. In other embodiments, the fiber diffuser can be formed by a fiber Bragg grating on the distal portion of the light guide. In some embodiments, the fiber diffuser can include a machined portion of the light guide, a laser-machined portion of the light guide, fiber Bragg gratings, a fused splicing, a fused splicing forming at least one internal mirror, and a splicing of two or more diffuse regions. Suitable materials for a fiber diffuser can include, but not be limited to, the materials of the core or cladding, ground glass, silver coated glass, gold coated glass, TiO2, and other materials that will scatter and not significantly absorbed the light wavelength of interest. One method that can be used to create a uniform diffuser in a light guide, optical component, or materials is to utilize scattering centers on the order of 50 nanometers to 5 micrometers in size. The scattering centers can have a distribution around 200 nanometers in size.

Light Sources

The light sources suitable for use herein can include various types of light sources including lasers and lamps. Suitable lasers can include short pulse lasers on the sub-millisecond timescale. In some embodiments, the light source can include lasers on the nanosecond (ns) timescale. The lasers can also include short pulse lasers on the picosecond (ps), femtosecond (fs), and microsecond (us) timescales. It will be appreciated that there are many combinations of laser wavelengths, pulse widths and energy levels that can be employed to achieve superheating in the balloon fluid of the catheters described herein. In various embodiments, the pulse widths can include those falling within a range including from at least 10 µs to 200 µs. In some embodiments, the pulse widths can include those falling within a range including from at least 20 µs to 100 µs. In other embodiments, the pulse widths can include those falling within a range including from at least 1 µs to 500 µs.

Exemplary microsecond lasers can include those within the UV to IR spectrum, spanning wavelengths of about 10 nanometers to 1 millimeter. In some embodiments, the light sources suitable for use in the catheter systems herein can include those capable of producing light at wavelengths of from at least 750 nm to 2000 nm. In some embodiments, the light sources can include those capable of producing light at wavelengths of from at least 700 nm to 3000 nm. In some embodiments, the light sources can include those capable of producing light at wavelengths of from at least 100 nm to 10 micrometers (µm). Microsecond lasers can include those having repetition rates of up to 200 kHz. In some embodiments, the laser can include a Q-switched thulium:yttrium-aluminum-garnet (Tm:YAG) laser. In some embodiments, the laser can include a neodymium:yttrium-aluminum-garnet (Nd:YAG), holmium:yttrium-aluminum-garnet (Ho:YAG), erbium:yttrium-aluminum-garnet (Er:YAG), excimer laser, helium-neon laser, carbon dioxide laser, as well as doped, pulsed, fiber lasers.

Acoustic Pressure Waves

The catheters herein can generate acoustic pressure waves having pressures in the range of 2 megapascals (MPa) to 25 MPa. The maximum pressure generated by a particular catheter will depend on the light source, the absorbing material, the propagation medium, and other factors. In some embodiments, the catheters herein can generate acoustic pressure waves having peak or maximum pressures in the range of 5 MPa to 20 MPa. In some embodiments, the catheters herein can generate acoustic pressure waves having peak pressures of about 1 MPa, 2 MPa, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, 21 MPa, 22 MPa, 23 MPa, 24 MPa, or 25 MPa. It will be appreciated that catheters herein can generate acoustic pressure waves having operating pressures or peak pressures that can fall within a range, wherein any of the forgoing numbers can serve as the lower or upper bound of the range, provided that the lower bound of the range is a value less than the upper bound of the range.

Therapeutic treatment can act via a fatigue mechanism or a brute force mechanism. For a fatigue mechanism, operating pressures would be about 0.5 MPa to 2 MPa, or about 1 MPa. For a brute force mechanism, operating pressures would be about 20 MPa to 30 MPa, or about 25 MPa. Pressures between the extreme ends of these two ranges may act upon a calcified lesion using a combination of a fatigue mechanism and a brute force mechanism.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

What is claimed is:

1. A catheter system for imparting pressure to induce fractures in a vascular lesion within or adjacent a vessel wall, comprising:
    a catheter that is configured to advance to the vascular lesion located within a blood vessel, the catheter comprising an elongate shaft and a balloon coupled to the elongate shaft, the balloon including a balloon wall, the balloon being configured to move between a collapsed configuration suitable for advancing the catheter through a patient's vasculature and a first expanded configuration suitable for anchoring the catheter in position relative to a treatment site; and
    a superheating system that is positioned at least partially within the balloon, the superheating system being configured to superheat a balloon fluid within the balloon to above its boiling point in less than ten milliseconds to achieve spontaneous vaporization of the balloon fluid and to generate inertial bubbles and acoustic pressure waves, the superheating system including a first light guide extending along the elongate shaft, the first light guide being configured to be in optical communication with a light source at a proximal portion of the first light guide, the first light guide including a first light window at a distal portion of the first light guide.

2. The catheter system of claim 1, wherein the first light guide is an optical fiber and the light source is a laser.

3. The catheter system of claim 1, further comprising a second light guide coupled to the elongate shaft, the second light guide being in optical communication with the light source.

4. The catheter system of claim 1, wherein the distal portion of the first light guide includes a diverting feature that is configured to direct light in the first light guide toward a side surface portion of the distal portion of the first light guide, the diverting feature including one of a reflecting element and a refracting element, the first light guide including the first light window that is positioned on the side surface portion.

5. The catheter system of claim 4, further comprising a thermally conductive photonic absorption layer disposed on the first light window, the thermally conductive photonic absorption layer being configured to be in optical communication with the light source, the thermally conductive photonic absorption layer being configured to (i) absorb a photonic energy from the first light guide and convert the photonic energy into thermal energy to achieve spontaneous vaporization of the balloon fluid within the balloon, and (ii) generate inertial bubbles and acoustic pressure waves.

6. The catheter system of claim 1, wherein the first light guide includes (i) a first fiber diffuser at the distal portion of the first light guide, and (ii) the first light window, the first fiber diffuser directing light from the first light guide to exit the first light guide at a side surface portion of the first light guide, the side surface portion being in optical communication with the first light window.

7. The catheter system of claim 1, wherein the distal portion of the first light guide includes (i) a plurality of light windows, and (ii) a plurality of fiber diffusers, each fiber diffuser directing light from the first light guide to exit the first light guide at a side surface portion of the first light guide, wherein each side surface portion is in optical communication with one of the plurality of light windows.

8. The catheter system of claim 7, wherein the plurality of light windows are axially spaced apart from one another by at least one intervening non-emitting portion of the first light guide.

9. The catheter system of claim 1, wherein the balloon fluid includes absorptive agents that selectively absorb light.

10. The catheter system of claim 1, wherein the first light guide is disposed in a spiral configuration about the elongate shaft.

11. A method for generating pressure to induce fractures in a vascular lesion within or adjacent a vessel wall of a blood vessel, comprising:

advancing a catheter to a vascular lesion location within the blood vessel, the catheter comprising a balloon coupled to an elongate shaft;

expanding the balloon from a collapsed configuration suitable for advancing the catheter through a patient's vasculature to a first expanded configuration suitable for anchoring the catheter in position relative to the vascular lesion location; and after expanding the balloon, superheating a balloon fluid to above its boiling point in less than ten milliseconds with a superheating system to achieve spontaneous vaporization of the balloon fluid and generation of inertial bubbles and acoustic pressure waves directed toward a balloon wall of the balloon, thereby imparting pressure upon the vascular lesion to induce fractures in the vascular lesion, the superheating system including a first light guide extending along the elongate shaft, the first light guide being configured to be in optical communication with a light source at a proximal portion of the first light guide, the first light guide including a first light window at a distal portion of the light guide.

12. The method of claim 11, wherein the step of superheating the balloon fluid includes superheating the balloon fluid to above its boiling point in more than 1 nanosecond and less than ten milliseconds.

13. The method of claim 11, wherein the first light guide is an optical fiber and the light source is a laser.

14. The method of claim 11, wherein the superheating system includes a second light guide coupled to the elongate shaft, the second light guide being in optical communication with the light source.

15. The method of claim 11, wherein the distal portion of the first light guide includes a diverting feature that is configured to direct light in the first light guide toward a side surface portion of the distal portion of the first light guide, the diverting feature including one of a reflecting element and a refracting element, the first light guide including the first light window that is positioned on the side surface portion.

16. The method of claim 15, further comprising the steps of (i) absorbing photonic energy from the first light guide with a thermally conductive photonic absorption layer that is disposed on the first light window and is in optical communication with the light source, (ii) converting the photonic energy into thermal energy to achieve spontaneous vaporization of the balloon fluid within the balloon, and (iii) generating inertial bubbles and acoustic pressure waves.

17. The method of claim 11, further comprising the step of directing light with a first fiber diffuser of the first light guide to exit the first light guide at a side surface portion of the first light guide, the side surface portion being in optical communication with the first light window of the first light guide.

18. A catheter system for imparting pressure to induce fractures in a vascular lesion within or adjacent a vessel wall, comprising:

a catheter configured to advance to the vascular lesion located within a blood vessel, the catheter comprising an elongate shaft and a balloon coupled to the elongate shaft;

wherein the balloon comprises a balloon wall and is configured to expand from a collapsed configuration suitable for advancing the catheter through a patient's vasculature to a first expanded configuration suitable for anchoring the catheter in position relative to a treatment site;

a superheating system configured to superheat a balloon fluid within the balloon to above its boiling point in less than ten milliseconds to achieve spontaneous vaporization of the balloon fluid and generate inertial bubbles and acoustic pressure waves, wherein the superheating system comprises a first light guide extending along the elongate shaft and configured to be placed in optical communication with a light source at a proximal portion of the first light guide, wherein a first light window is in optical communication with the balloon fluid; and a thermally conductive photonic absorption layer in optical communication with the first light window and the light source, wherein the thermally conductive photonic absorption layer is configured to absorb a photonic energy from the light guide and convert the photonic energy into thermal energy to achieve spontaneous vaporization of a balloon fluid within the balloon and to generate inertial bubbles and acoustic pressure waves.

19. The catheter system of claim 18, wherein the first light guide is an optical fiber and the light source is a laser.

20. The catheter system of claim 18, wherein the thermally conductive photonic absorption layer is disposed on the first light window.

\* \* \* \* \*